US008652032B2

(12) United States Patent
Yamane

(10) Patent No.: US 8,652,032 B2
(45) Date of Patent: Feb. 18, 2014

(54) PLUG BODY AND ENDOSCOPE

(75) Inventor: Kenji Yamane, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 134 days.

(21) Appl. No.: 13/432,012

(22) Filed: Mar. 28, 2012

(65) Prior Publication Data
US 2012/0253128 A1 Oct. 4, 2012

(30) Foreign Application Priority Data

Mar. 29, 2011 (JP) ................. P2011-072280

(51) Int. Cl.
A61B 1/00 (2006.01)
A61M 5/178 (2006.01)

(52) U.S. Cl.
USPC ...................... 600/154; 604/167.05

(58) Field of Classification Search
USPC ................. 600/104, 114, 154; 604/111, 604/167.01–167.06
See application file for complete search history.

(56) References Cited

U.S. PATENT DOCUMENTS 4,809,679 A * 3/1989 Shimonaka et al. .......... 600/154
8,333,693 B2 * 12/2012 Hamazaki ..................... 600/154
2003/0028096 A1 2/2003 Niwa et al.

FOREIGN PATENT DOCUMENTS

| JP | 2-283345 A | 11/1990 |
| JP | 3-42275 A | 2/1991 |
| JP | 2006-55446 A | 3/2006 |
| JP | 2008-43774 A | 2/2008 |

* cited by examiner

Primary Examiner — Alireza Nia
Assistant Examiner — Timothy J Neal
(74) Attorney, Agent, or Firm — Birch, Stewart, Kolasch & Birch, LLP

(57) ABSTRACT

A forceps plug includes a tubular plug main body, and a tubular fixing member rotatably held on the outer periphery of the plug main body. The inner peripheral surface of the fixing member is provided with a pair engaging claws. A ratchet mechanism that allows the fixing member to move to an incorporated location, an attachment position, a fixed position, and a removal position in order, but stops further movement to a position where the fixing member has moved once is provided between the inner peripheral surface of the plug main body and the outer peripheral surface of the fixing member. Since the fixing member of the used forceps plug removed from a opening is stopped from being to the fixed position by the ratchet mechanism, the fixing member cannot be fixed to the opening. Reuse of the used forceps plug can be made impossible without being accompanied by destruction.

20 Claims, 44 Drawing Sheets

PLUG BODY AND ENDOSCOPE

BACKGROUND OF THE INVENTION

1. Field of the Invention

The present invention relates to a disposable plug body that is attached to the opening portion of a channel of an endoscope and an endoscope equipped with the plug body.

2. Description of the Related Art

Until now, in the medical field, an insertion part of an endoscope is inserted into the body of a patient to perform not only the observation of the inside of the body, but also various kinds of treatments on the parts being observed. Specifically, various kinds of treatments, such as resection or collection of observed parts, are performed by inserting various treatment tools, such as forceps and a resection implement, through a forceps channel within the insertion part from a forceps port opening (opening portion) provided at a manipulating part of the endoscope, and projecting the treatment tools from the tip of the insertion part.

A forceps plug through which a treatment tool can be inserted when a treatment is performed is mounted on the forceps port opening (refer to JP1991-042275A (JP-H03-042275A) and JP1990-283345A (JP-H02-283345A)). This forceps plug prevents body fluid, filth, air, or the like in the body from flowing back within the forceps channel and leaking out to the outside from the forceps port opening, due to changes in internal pressure within the body. As such a forceps plug, a disposable forceps plug in which reuse is impossible is general so as to be replaced with a new one for each use from a viewpoint of prevention of infection due to adhesion of body fluid or the like.

JP2008-043774A discloses a forceps plug that becomes removable from the forceps opening by breaking a portion of the plug body. Additionally, JP2006-055446A discloses a forceps plug including a plug main body and an engaging portion that engages a forceps port opening and having a notch formed therebetween. In this forceps plug, the portion between the plug main body and the engaged portion is broken by the pulling manipulation of the plug main body, and thereby reuse of the forceps plug becomes impossible. In the forceps plugs of JP2008-043774A and JP2006-055446A, reuse becomes impossible because the removal from the forceps port opening is accompanied by destruction. As a result, a used forceps plug is prevented from being erroneously reused.

SUMMARY OF THE INVENTION

In the forceps plugs of Patent Documents JP2008-043774A and JP2006-055446A, the removal from the forceps port opening is accompanied by destruction. Thus, there is a concern that broken pieces produced by this destruction might enter the forceps channel. In this case, a problem occurs in that washing or disinfection treatment within the forceps channel. Additionally, in the forceps plugs of JP2008-043774A and JP2006-055446A, it is necessary to form a weakened part, such as a notch. For this reason, when the forceps plug is attached to the forceps port opening, there is a concern that a weakened part may be erroneously destroyed.

The present invention has been made in view of the above-mentioned problems and an object of the present invention is to provide a plug body for an endoscope, such as a forceps plug, in which reuse becomes impossible without being accompanied by destruction, and an endoscope equipped with the plug body.

In order to achieve the above object, the present invention provides a plug body provided on the external surface of an endoscope and attached to a tubular opening portion that leads to a channel within the endoscope. The plug body includes a tubular plug main body into which the opening portion is inserted; a tubular fixing member rotatably or slidably held in the plug main body, having an insertion hole into which the opening portion is inserted, and a claw provided on the inner peripheral surface that forms the insertion hole, and movable to respective positions including an engagement position where the claw engages an engaged portion provided at an outer periphery of the opening portion inserted into the insertion hole, and one or more non-engagement positions where the claw does not engage the engaged portion, and a ratchet mechanism provided in mutually opposed faces of the plug main body and the fixing member, permitting the fixing member to be moved to the respective positions in predetermined order, and stopping further movement of the fixing member to a position where the fixing member has moved once. In addition, the tubular shapes means a hollow tubular shape, and the cross-section orthogonal to the axis direction thereof is, for example, circular, elliptical, polygonal, or the like.

Preferably, the non-engagement position includes a removal position when the plug main body is removed from the opening portion, and the ratchet mechanism permits the fixing member to move in order of the engagement position and the removal position.

Preferably, the fixing member is rotatably held on the outer periphery of the plug main body, and has an extending portion that extends to the downward side toward a deep side of an opening of the opening portion beyond the plug main body, and the extending portion is provided with the claw, the non-engagement position includes an attachment position when the opening portion is inserted into the insertion hole, and the ratchet mechanism permits the fixing member to be rotated in a predetermined rotational direction in order of the attachment position, the engagement position, and the removal position and stops the rotation of the fixing member in a reverse rotational direction opposite to the predetermined rotational direction.

Preferably, the ratchet mechanism has a rotation stop that stops the fixing member from further rotating from the removal position to the predetermined rotational direction.

Preferably, an unused mark indicating unused is provided at a position where the mark is exposed to the outside when the fixing member is at the attachment position, or at a position where the mark is covered with the plug main body when the fixing member is at the engagement position or the removal position, on the external surface of the fixing member.

Preferably, a used mark indicating used is provided at a position where the mark is exposed to the outside when the fixing member is at the removal position, or at a position where the mark is covered with the plug main body when the fixing member is at the attachment position or the engagement position, on the external surface of the fixing member.

Preferably, the fixing member is held on the inner periphery of the plug main body so as to be slidable along the axial direction of the opening portion, and the removal position is a position offset to the deep side of an opening of the opening portion beyond the engagement position, and the inner periphery of the plug main body is provided with an engagement releasing portion that releases the engagement between the claw and the engaged portion when the fixing member has relatively moved to the removal position from the engagement position with the removal manipulation of pulling the plug main body toward the near side of the opening of the opening portion.

Preferably, the fixing member has an arm portion formed by cutting out a portion of the fixing member, and extending a considerable length in the axial direction, and having an end on the downward side as a free end, and the free end is provided with the claw, the engagement releasing portion has a shape that protrudes toward the claw from the position offset to the downward side with respect to the claw, when the fixing member has moved to the removal position, the engagement between the claw and the engaged portion is released as the engagement releasing portion presses the claw to elastically deform the arm portion in a direction in which the claw is kept away from the outer periphery of the opening portion.

Preferably, the fixing member has an arm portion formed by cutting out a portion of the fixing member, and extending a considerable length in the axial direction, and having an end on the downward side as a free end, one face of the free end facing the opening portion is provided with the claw, and the other face opposite to the one face is provided with a protruding portion that protrudes toward the inner periphery of the plug main body, and receives the pressure from the inner periphery to elastically deform the arm portion in a direction toward the outer periphery of the opening portion, thereby maintaining a state where the claw is engaged with the engaged portion, the engagement releasing portion is a fitting groove formed in the inner periphery of the plug main body and engaged with the protruding portion when the fixing member has moved to the removal position, and the engagement between the claw and the engaged portion is released as the arm portion restores to its original shape when the protruding portion fits to the fitting groove.

Preferably, the fixing member is rotatably held on the inner periphery or outer periphery of the plug main body, the non-engagement position includes an attachment position when the opening portion is inserted into the plug main body, the ratchet mechanism permits the fixing member to be rotated in a predetermined rotational direction in order of the attachment position and the engagement position, and stops the rotation of the fixing member in a reverse rotational direction opposite to the predetermined rotational direction, and when the removal manipulation of pulling the plug main body to the near side of the opening of the opening portion is performed in a state where the fixing member is at the engagement position, the claw is pressed against and deflected by the engaged portion located on the near side thereof, and thereby, the engagement between the claw and the engaged portion is released to remove the plug main body from the opening portion.

Preferably, the fixing member has an extending portion that is rotatably held on the outer periphery of the plug main body and extends closer to the direction of the opening portion than the plug main body, and the claw is provided at the extending portion.

Preferably, the fixing member is rotatably held on the inner periphery of the plug main body, the claw engages a guide groove that extends in an oblique direction from a opening portion tip position offset in the reverse rotational direction with respect to the engaged portion to the engaged portion, in the tip of the opening portion when the fixing member is at the attachment position, and when the attachment manipulation of pressing the plug main body against the opening portion after the engagement between the claw and the guide groove is performed, the claw moves to the engaged portion along the guide groove, and the fixing member rotates to the engagement position from the attachment position with the movement of the claw.

Preferably, the ratchet mechanism is provided with a rotation stop that stops the fixing member from further rotating from the engagement position to the predetermined rotational direction.

Preferably, the present invention provides an endoscope including a manipulating part connected to a base end portion of an insertion part to be inserted into a sample; a tubular opening portion that is provided in the manipulating part and leads to a channel inserted into the insertion part; and the plug body according to any one of the above inventions attached to the opening portion.

In the plug body and the endoscope of the present invention, the fixing member held by the plug main body so as to be movable to respective positions including the engagement position where the fixing member engages the outer periphery of the opening portion, and one or more non-engagement positions where the fixing member does not engage the outer periphery of the opening portion is stopped from moving again to a position where the fixing member has moved once by the ratchet mechanism. Thus, the fixing member cannot return to its original position after the removal of the plug body. Thereby, since the used plug body cannot be fixed or attached to the opening portion, reuse of the used plug body can be prevented without being accompanied by the destroying of the plug body. As a result, occurrence of troubles, such as entering of broken pieces produced by the destruction into the forceps channel can be prevented. Additionally, since it also becomes unnecessary to form a weakened part, such as a notch, in the plug body, there is not a concern that the weakened part is erroneously destroyed when the plug body is attached to the opening portion.

DESCRIPTION OF THE PREFERRED EMBODIMENTS

[First Embodiment]

Figure 1:
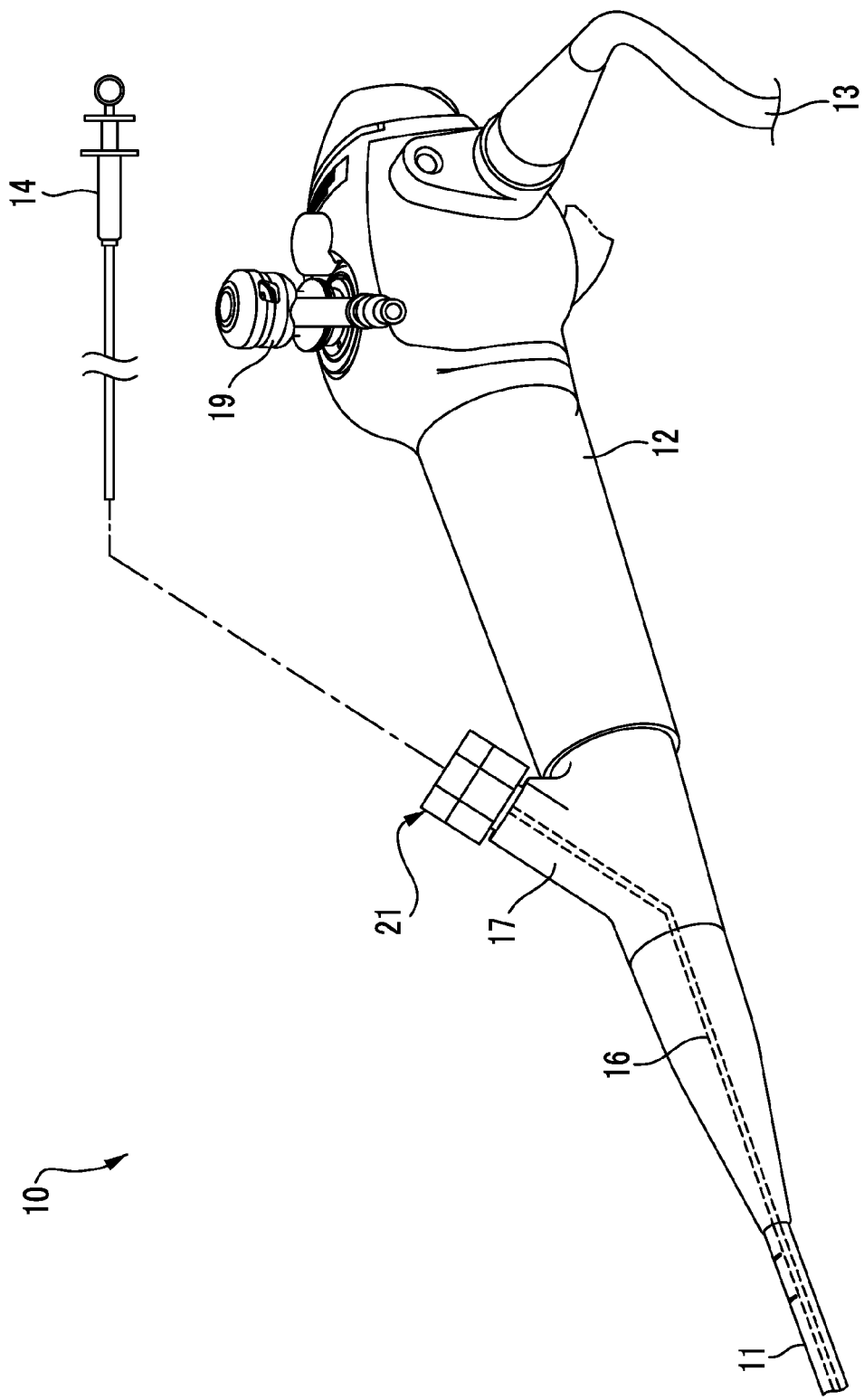
FIG. 1 is a perspective view of an endoscope.

As shown in FIG. 1, an endoscope 10 is, for example, a bronchoscope to be inserted into the trachea, and includes an insertion part 11 to be inserted into the trachea, a manipulating part 12 continuously provided at a base end portion of the insertion part 11, and a universal cord 13 connected to the manipulating part 12. The universal cord 13 is connected to a processor device, a light source device, or the like that is not shown.

A forceps channel 16 for allowing a treatment tool 14, such as forceps, to be inserted therethrough is disposed within the insertion part 11. One end of the forceps channel 16 opens at the tip face of the insertion part 11, and the other end thereof is connected to a forceps port 17 provided at the manipulating part 12. Additionally, the forceps channel 16 is also used as a path for suctioning body fluids, such as blood, solids, such as filth in the body, or the like from the opening of the tip face of the insertion part 11. A suction channel (not shown) that branches from the forceps channel 16 is disposed within the manipulating part 12, and this suction channel is connected to a suction button 19 provided at the manipulating part 12.

The suction button 19 is connected to a negative pressure source (not shown) out of the manipulating part 12. The suction button 19 switches the communication/blocking between the suction channel and the negative pressure source by pressing manipulation or release of the pressing manipulation.

Figure 2:
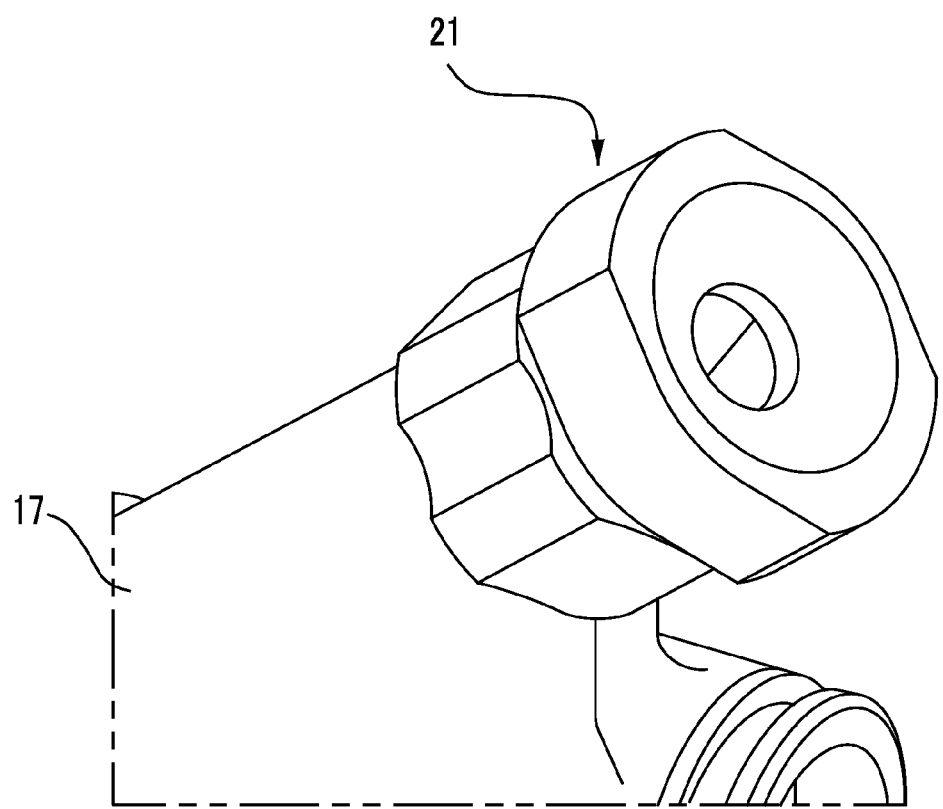
FIG. 2 is a perspective view of a forceps plug of a first embodiment.

As shown in FIG. 2, the forceps port 17 is mounted with a disposable forceps plug (plug body) 21 through which the treatment tool 14 can be inserted via a forceps port opening (hereinafter simply referred to as an opening; refer to FIGS. 3 to 5) 20 corresponding to the opening portion of the present invention. The forceps plug 21 prevents body fluid, filth, air, or the like in the body from flowing back within the forceps channel 16 and leaking out to the outside from the opening 20, when a treatment is performed by the treatment tool 14.

Figure 3:
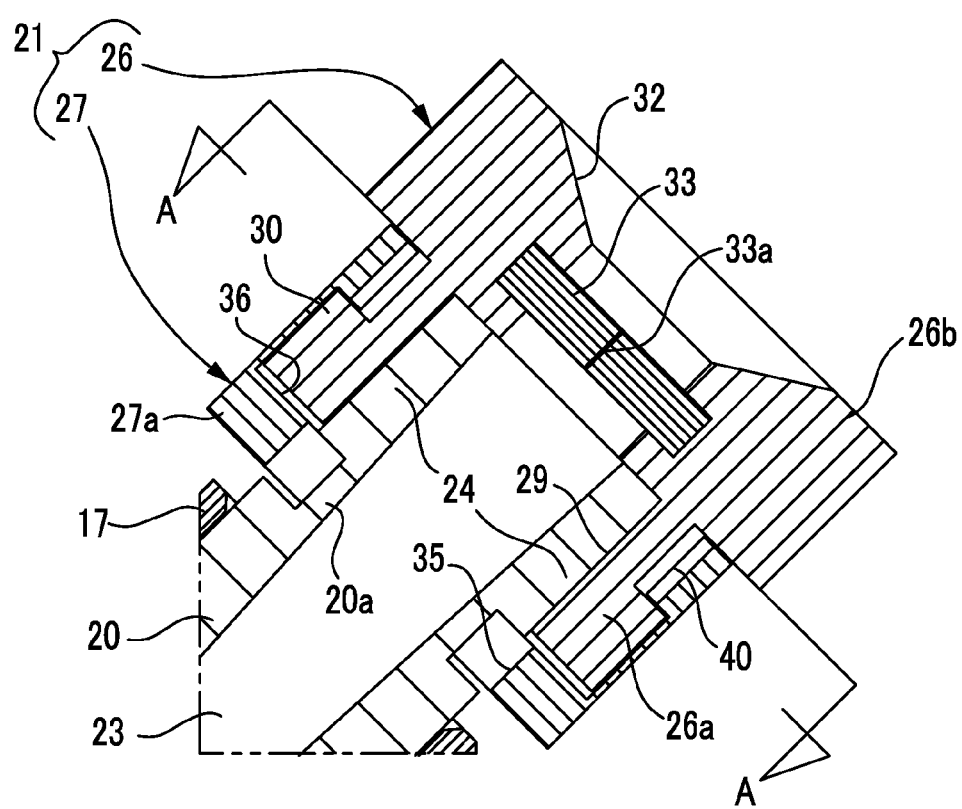
FIG. 3 is a cross-sectional view of an opening and a forceps plug.
Figure 4:
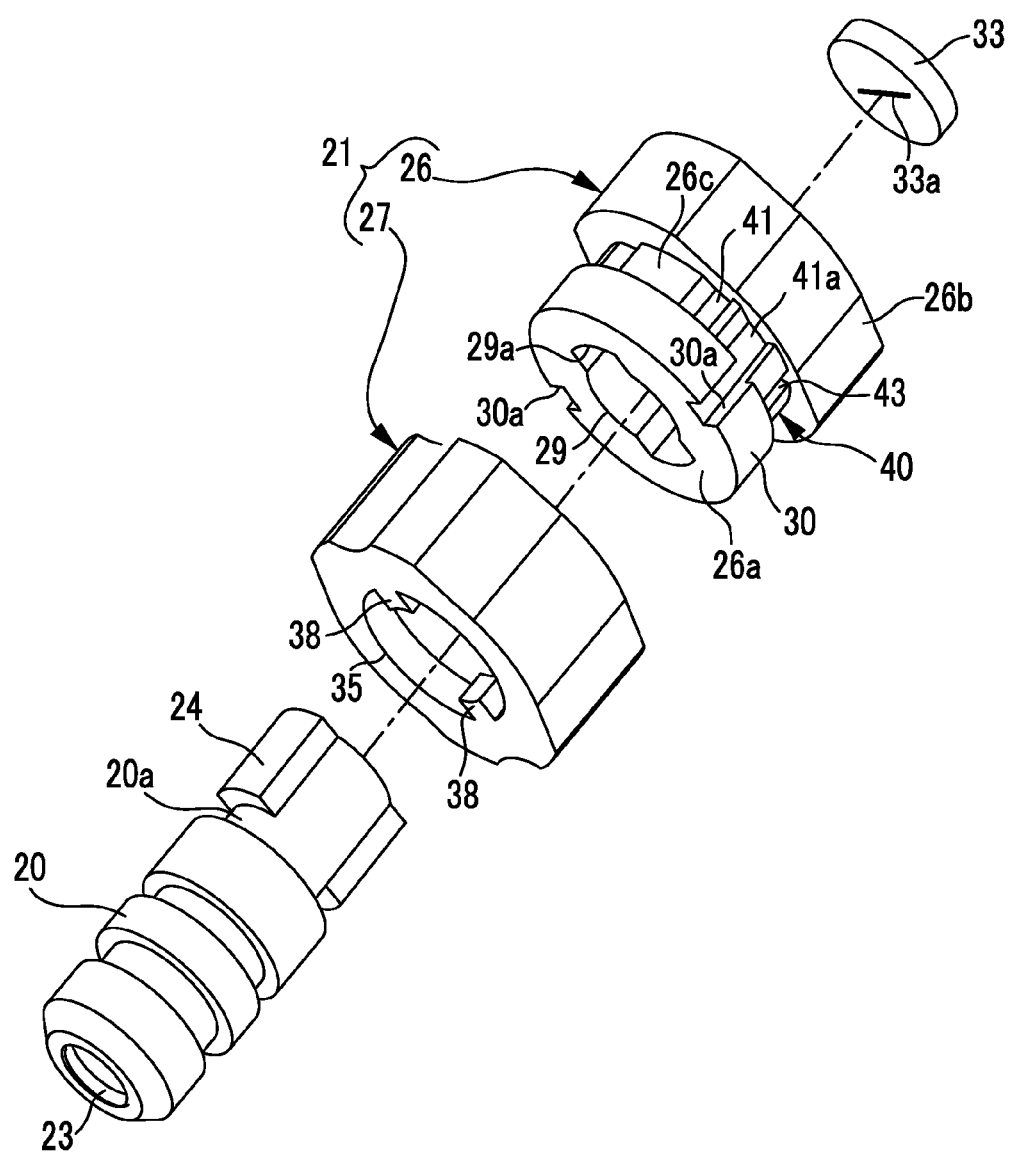
FIG. 4 is an exploded perspective view of the forceps plug seen from the downward side.
Figure 5:
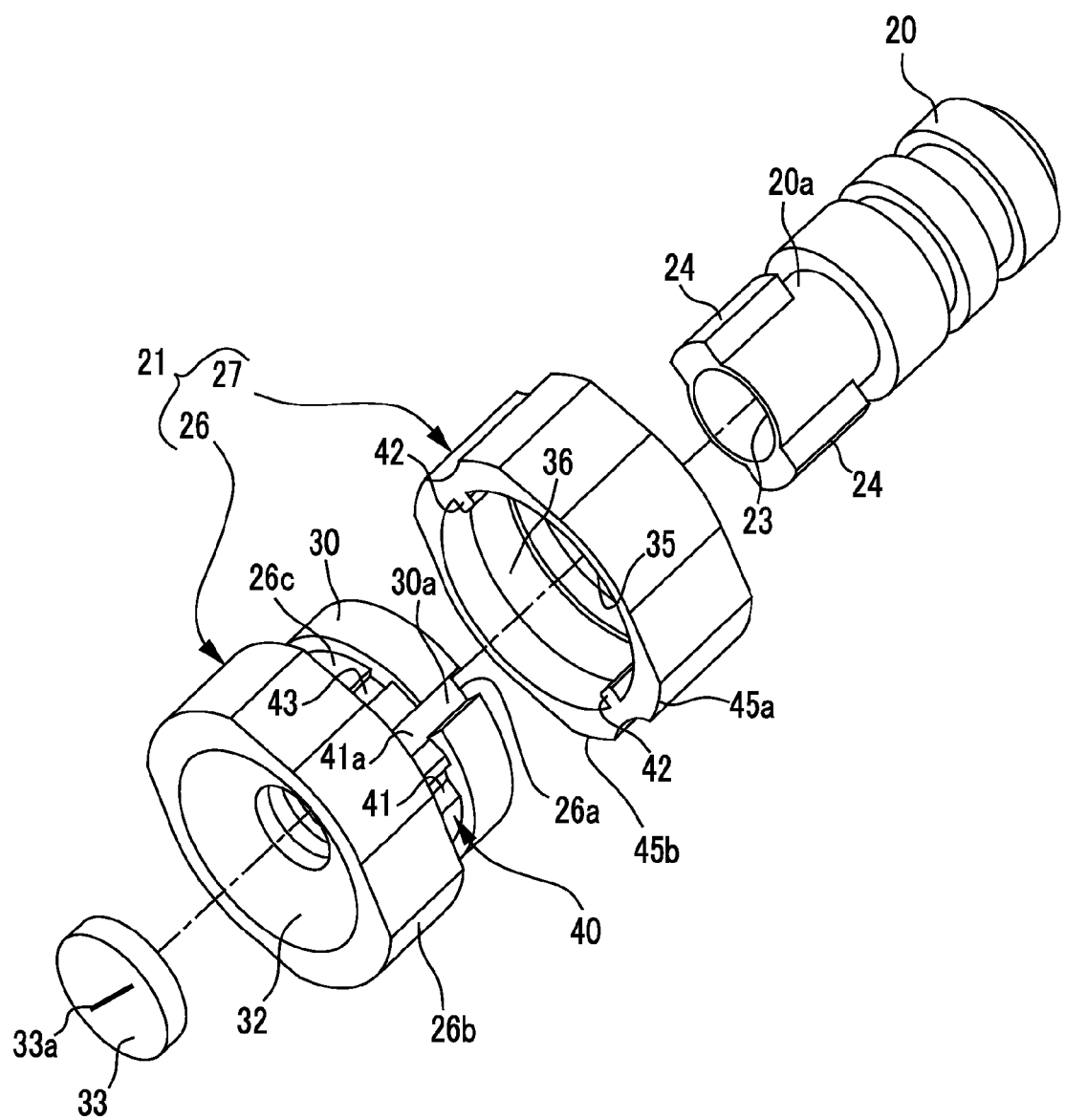
FIG. 5 is an exploded perspective view of the forceps plug seen from the downward side.

As shown in FIG. 3 or 5, the opening 20 has an internal conduit 23 that leads to the forceps channel 16, and is fixed to an aperture of the forceps port 17. A tip portion (hereinafter referred to as an opening tip portion) 20a of the opening 20 protruding from this aperture is formed so as to have a slightly smaller diameter than other portions.

A pair of protrusions 24 are formed at 180° to each other in the outer peripheral surface of the opening tip portion 21a. A portion of the forceps plug 21 engages the protrusions 24. Hereinafter, a direction toward the deep side where the internal conduit is present from the opening of the opening tip portion 20a is referred to as "downward", and a direction toward the near side where the internal conduit is not present from the opening of the tip portion 20a is referred to as "upward". Additionally, the end portion and end face of each portion of the opening 21 on the downward side are referred to as a lower end portion and a lower end face, respectively, and the end portion and end face of each portion on the upward side are referred to an upper end portion and an upper end face, respectively.

The forceps plug 21 is formed from resin materials, such as plastics. The forceps plug 21 includes a tubular plug main body 26, and a tubular fixing member 27 rotatably held on the outer periphery of the plug main body 26.

The plug main body 26 includes a fixing member holding portion (hereinafter simply referred to as a holding portion) 26a that rotatably holds the fixing member 27, and a head 26b continuously provided at the upper end of the holding portion 26a. The holding portion 26a has an inside insertion hole 29 into the opening tip portion 20a is inserted. Additionally, a flange 30 is formed at a lower end portion of the outer peripheral surface of the holding portion 26a.

The depth of the inside insertion hole 29 is formed so as to become the same as the length of the opening 20 in the protrusions 24 in the axial direction (hereinafter referred to as a opening axial direction). Additionally, protrusion insertion holes 29a into which the protrusions 24 are inserted are formed integrally with the inside insertion hole 29.

A treatment tool entrance 32 coaxial with the inside insertion hole 29 is formed in the head 26b. The diameter of the treatment tool entrance 32 is formed so as to be slightly smaller than the diameter of the inside insertion hole 29. Thereby, an opening peripheral edge portion at the lower end of the treatment tool entrance 32 abuts on the opening tip portion 20a inserted into the inside insertion hole 29. A slit plate 33 made of an elastic material so as to plug up the inside is provided within the treatment tool entrance 32.

The slit plate 33 has a slit 33a at the center thereof. The slit 33ab is brought into a close contact state by an elastic force to hold a watertight or airtight state when the treatment tool 14 is not inserted therethrough. On the other hand, the slit 33a is brought into a state where the inner peripheral surface of the slit is brought into close contact with the outer peripheral surface of the treatment tool 14 by an elastic force, to prevent the leakage caused by the backflow of a body fluid or the like, in a state where the treatment tool 14 is inserted therethrough. The treatment tool entrance 32 and the slit 33a are arranged coaxially with the internal conduit 23 when the opening tip portion 20a is inserted into the inside insertion hole 29. For this reason, the treatment tool 14 is inserted into the forceps channel 16 through the treatment tool entrance 32, the slit 33a, and the internal conduit 23.

The fixing member 27 has an outside insertion hole 35 located outside the inside insertion hole 29. The holding portion 26a is inserted from an opening at the upper end of the outside insertion hole 35, and the opening tip portion 20a and the protrusions 24 are inserted from the opening at the lower end of the outside insertion hole. An engagement groove 36 that the flange 30 engages is formed in the inner peripheral surface of the fixing member 27 that forms the outside insertion hole 35 along the circumferential direction thereof. Thereby, the fixing member 27 is rotatably held on the outer periphery of the holding portion 26a.

Additionally, the fixing member 27 has an extending portion 27a whose lower end portion extends downward beyond the lower end portion of the plug main body 26. The inner peripheral surface of extending portion 27a is formed with a pair of engaging claws 38 that faces each other. The engaging claws 38 protrude toward the outer peripheral surface of the opening tip portion 20a, and plugs up portions of the openings of the protrusion insertion holes 29a.

A ratchet mechanism 40 that regulates the rotation of the fixing member 27 is provided in portions of mutually opposed faces of the holding portion 26a and the fixing member 27. The ratchet mechanism 40 includes a plurality of ratchet grooves 41 formed at an upper end portion (hereinafter referred to as an outer peripheral surface upper end portion) 26c of the outer peripheral surface of the holding portion 26a, a pair of ratchet claws 42 formed at 180° to each other at an upper end portion of the inner peripheral surface of the fixing member 27, and engaging the ratchet grooves 41, and a pair of rotation stop grooves 43 formed at 180° to each other in the outer peripheral surface upper end portion 26c.

The ratchet grooves 41 have a shape over which the ratchet claws 42 can ride when the fixing member 27 is rotated clockwise (predetermined rotational direction) as seen from the near side of the forceps plug 21, but that locks the ratchet claws 42 when the fixing member is rotated counterclockwise. Thereby, the rotational direction of the fixing member 27 is limited only to the clockwise direction. Hereinafter, the clockwise direction is based on when seen from the near side of the forceps plug.

A pair of guide grooves 30a that leads to a pair of ratchet grooves 41 formed at 180° to each other, respectively, is formed in the flange 30. The guide grooves 30a guide the ratchet claws 42 to the ratchet grooves 41 when the fixing member 27 is incorporated into the plug main body 26. Hereinafter, the ratchet grooves 41 that lead to the guide grooves 30a are referred to "incorporating ratchet grooves 41a".

The rotation stop grooves 43 are formed at positions to pinch the two ratchet grooves 41 therebetween in the clockwise direction with respect to the incorporating ratchet grooves 41a. The rotation stop grooves 43 lock the ratchet claws 42 to stop the clockwise rotation/counterclockwise rotation of the fixing member 27.

Such a ratchet mechanism 40 allows the fixing member 27 to rotate in the clockwise direction, to move to a total of following four positions, that is, an incorporation position, an attachment position, a fixed position, and a removal position in order, but stops further movement to a position where the fixing member has moved once. In addition, the fixed position corresponds to the engagement position of the present invention, and the other three positions correspond to the nonengagement position of the present invention.

Figure 6:
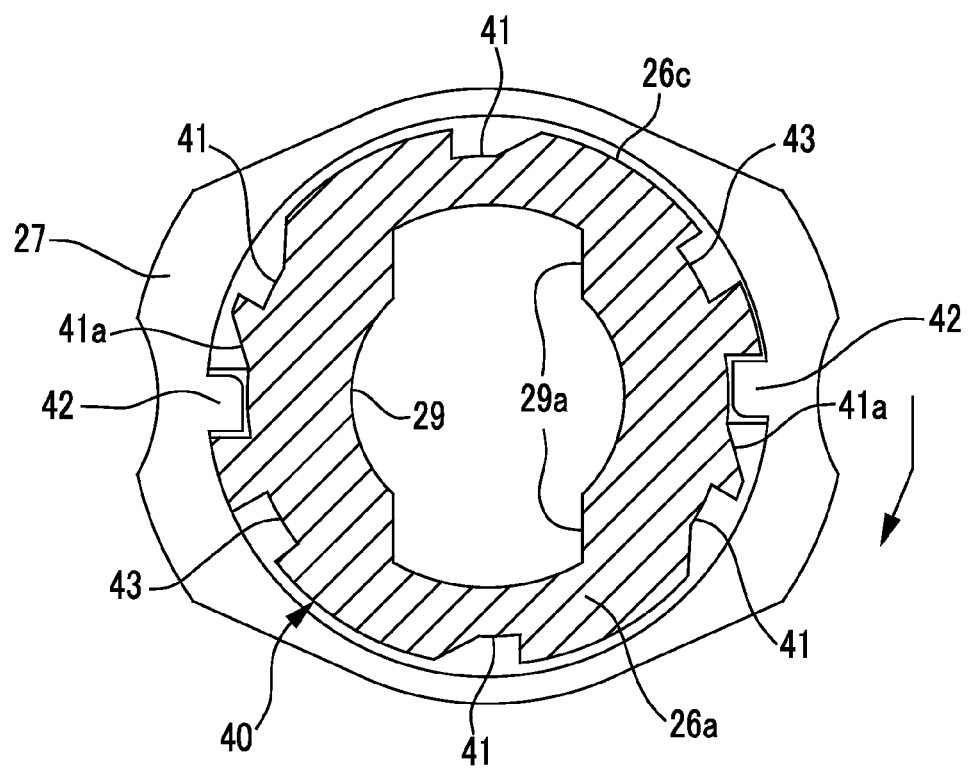
FIG. 6 is a cross-sectional view along line A-A in FIG. 3, showing a state where a fixing member is set in its incorporated location.

As shown in FIG. 6, the incorporation position is a position where the ratchet claws 42 guided from the guide grooves 30a engage the incorporating ratchet grooves 41a. Accordingly, this incorporation position is a position that is first set first when the fixing member 27 is incorporated into the plug main body 26.

Figure 7:
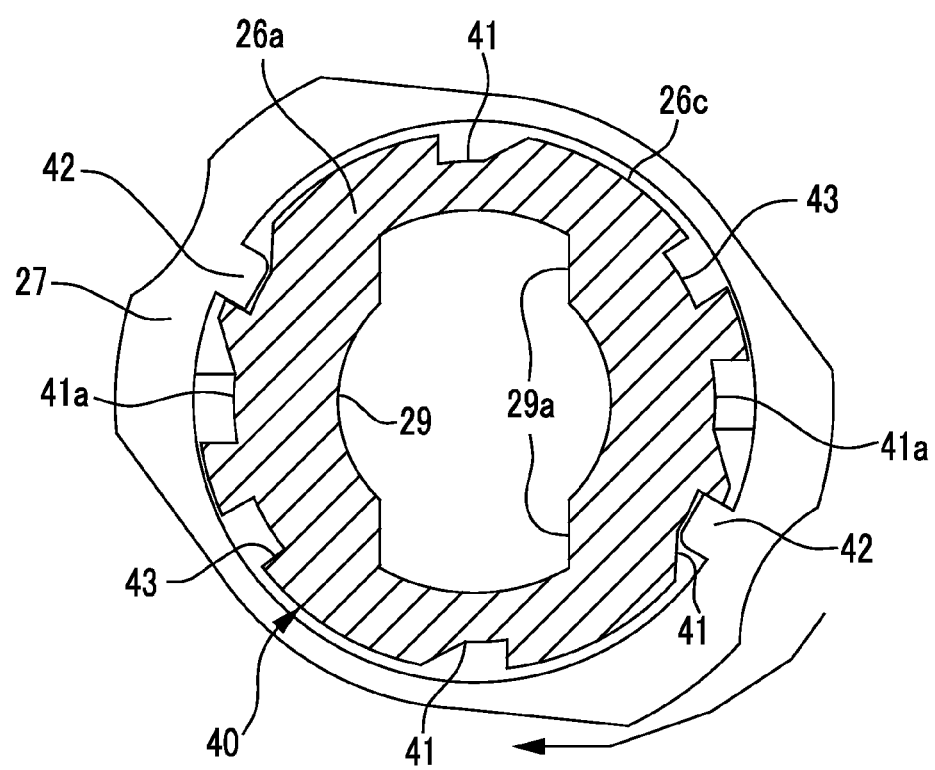
FIG. 7 is a cross-sectional view along line A-A in FIG. 3, showing a state where the fixing member is set at an attachment position.

As shown in FIG. 7, the attachment position is a position where the ratchet claw 42 engages one adjacent ratchet groove 41 in the clockwise direction with the incorporating ratchet grooves 41a. In the attachment position, the engaging claws 38 are retreated from on the protrusion insertion holes 29a. This attachment position is a position set when the forceps plug 21 is attached to the opening tip portion 20a. In addition, the fixing member 27 is set at the attachment position at the time of shipment of the forceps plug 21.

Figure 8:
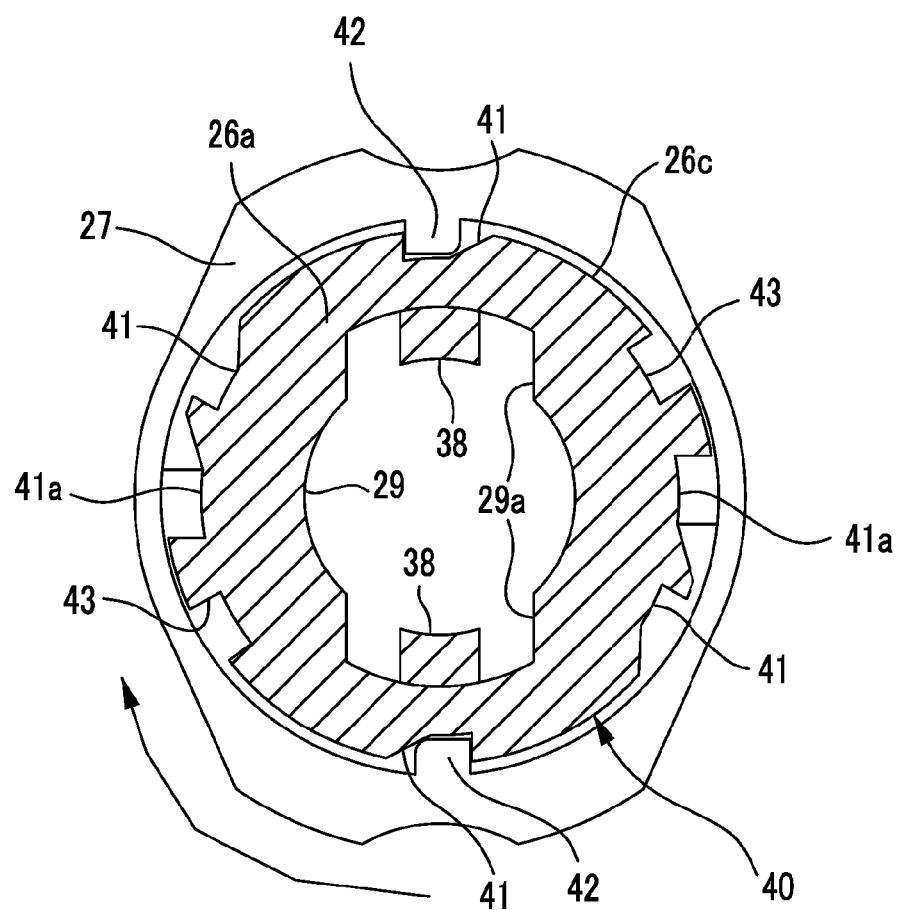
FIG. 8 is a cross-sectional view along line A-A in FIG. 3, showing a state where the fixing member is set at a fixed position.

As shown in FIG. 8, a fixed position is a position where the ratchet claws 42 engage two adjacent ratchet grooves 41 in the clockwise direction with respect to the incorporating ratchet grooves 41a. In the fixed position, the engaging claws 38 cover portions of the protrusion insertion holes 29a. This fixed position is a position set when the forceps plug 21 is fixed to the opening tip portion 20a.

Figure 9:
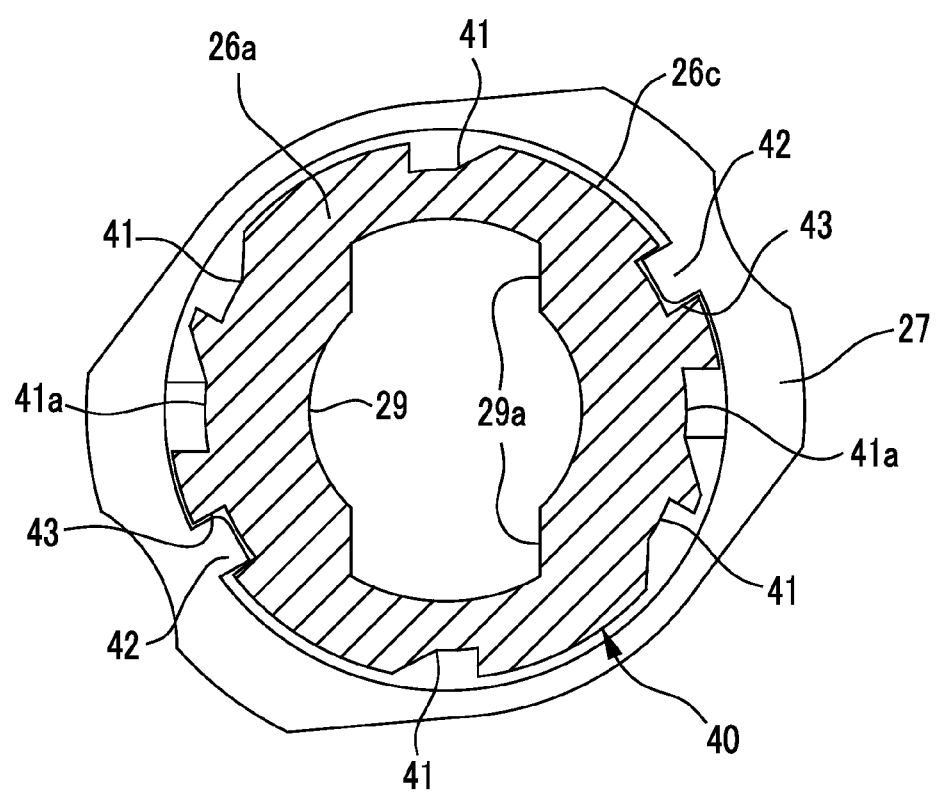
FIG. 9 is a cross-sectional view along line A-A in FIG. 3, showing a state where the fixing member is set at a removal position.

As shown in FIG. 9, the removal position is a position where the ratchet claws 42 engage the rotation stop grooves 43. In the removal position, the engaging claws 38 are retreated from on the protrusion insertion holes 29a. This removal position is a position set when the forceps plug 21 is removed from the opening tip portion 20a.

Returning to FIG. 5, an unused mark 45a indicating that the forceps plug 21 is unused and a used mark 45b indicating the forceps plug 21 is used are formed at the upper end face of the fixing member 27. The unused mark 45a is exposed to the outside when the fixing member 27 is at the attachment position, and is covered with the plug main body 26 at the other positions. The used mark 45b is exposed to the outside when the fixing member 27 is at the removal position, and is covered with the plug main body 26 at the other positions. In addition, the form and forming position of the unused mark 45a and the used mark 45b may be appropriately changed.

Next, the attachment and removal processing of the forceps plug 21 of the above configuration will be described. The fixing member 27 of the forceps plug 21 is set at the attachment position in the stage of the shipment from a maker. Thereby, the plug main body 26 and the fixing member 27 become inseparable. Additionally, since the unused mark 45a is exposed to the outside when the fixing member 27 is set at the attachment position, it is possible to easily discriminate that the forceps plug 21 is unused.

Figure 10:
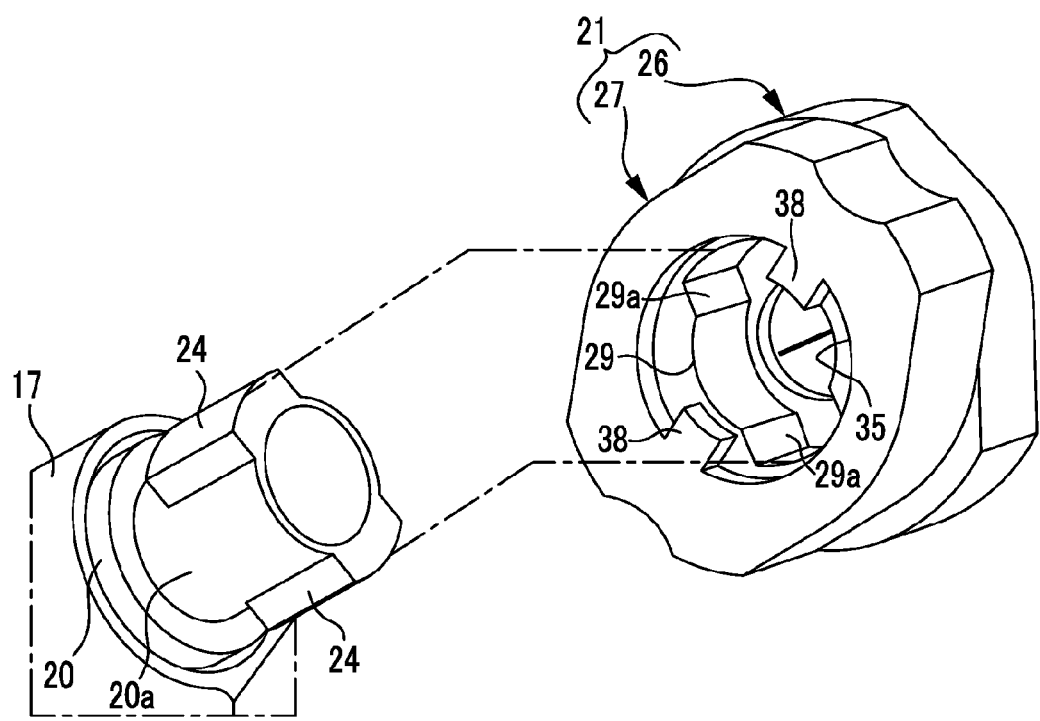
FIG. 10 is a perspective view of the plug before attachment to the opening.

As shown in FIG. 10, positioning of the forceps plug 21 is performed so that the center of the outside insertion hole 35 and the center of the inside insertion hole 29 coincide with the center of the opening tip portion 20a, and the protrusions 24 and the protrusion insertion holes 29a coincide with each other. After this positioning, the forceps plug 21 is pressed against the opening tip portion 20a. Thereby, the opening tip portion 20a and the protrusions 24 are inserted into the inside insertion hole 29 and the protrusion insertion holes 29a through the outside insertion hole 35, respectively.

Figure 11:
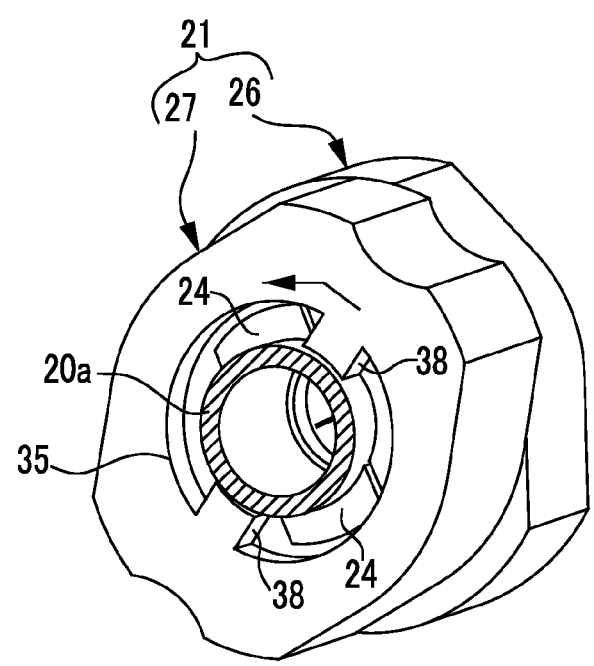
FIG. 11 is a perspective view of the forceps plug seen from the downward side after attachment to the opening.
Figure 12:
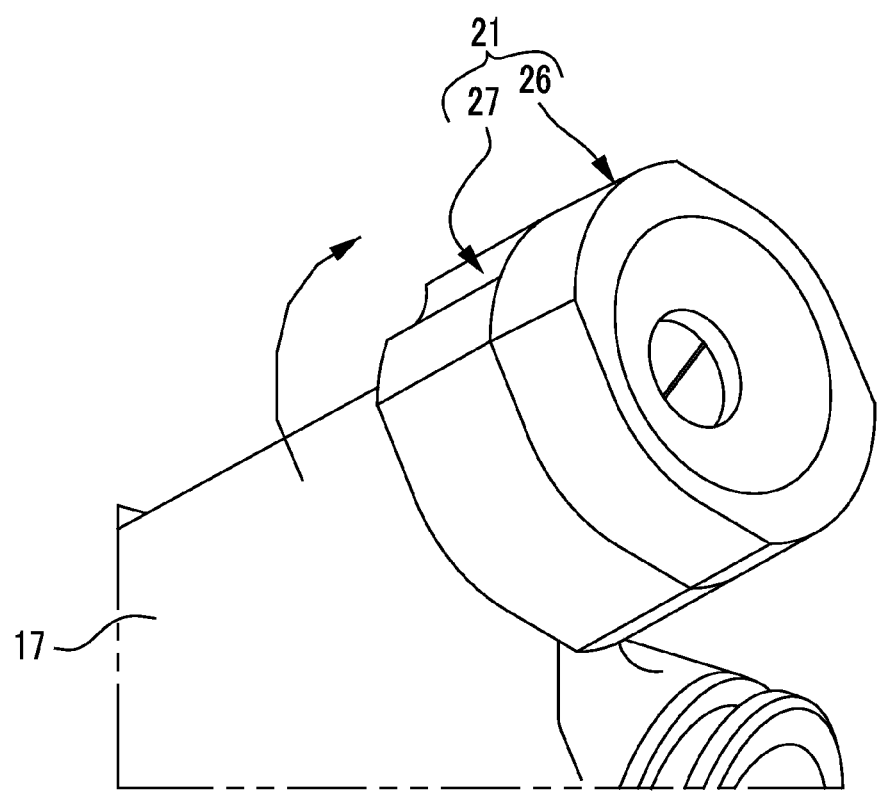
FIG. 12 is a perspective view of the forceps plug when the fixing member is set at the fixed position.
Figure 13:
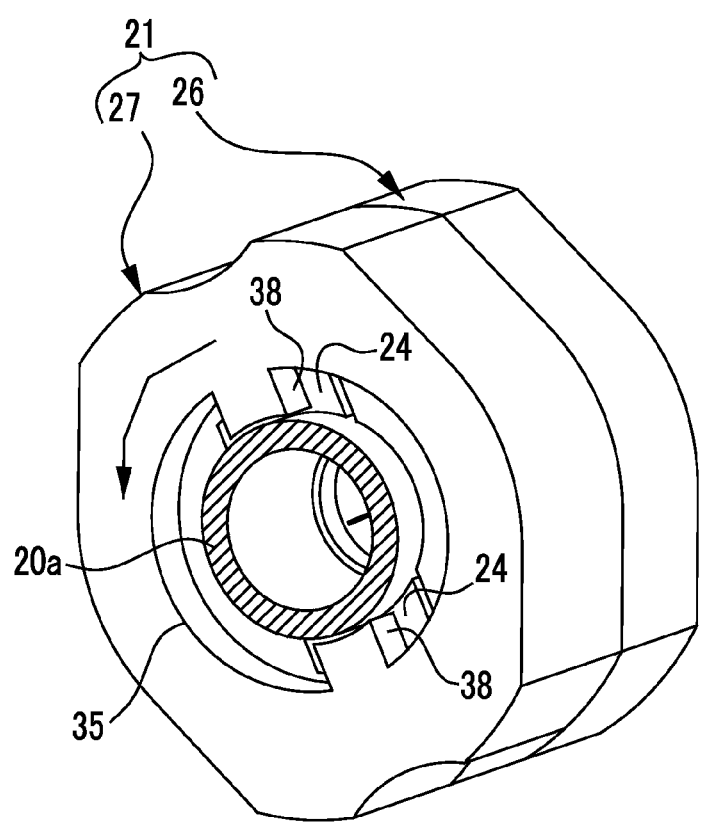
FIG. 13 is a perspective view of the forceps plug of FIG. 12 seen from the downward side.

Next, as shown in FIG. 11, the fixing member 27 is rotated clockwise (counterclockwise in the drawing) from the attachment position, and is sets at the fixed position as shown in FIG. 12. Thereby, as shown in FIG. 13, the engaging claws 38 are t moved so as to cover portions of the protrusion insertion holes 29a, and the engaging claws 38 and the protrusions 24 engage each other. The forceps plug 21 is fixed to the opening 20 in this way.

The attachment processing of the forceps plug 21 is completed above. Then, after the insertion part 11 is inserted into the trachea of a patient, the treatment tool 14 is inserted into the forceps channel 16 from the forceps plug 21, and various kinds of treatment are performed. After all examination and medical treatment by the endoscope 10 including treatment by the treatment tool 14 (simply referred to as endoscopic examination and treatment) are completed, the removal processing of the forceps plug 21 is started.

Figure 14:
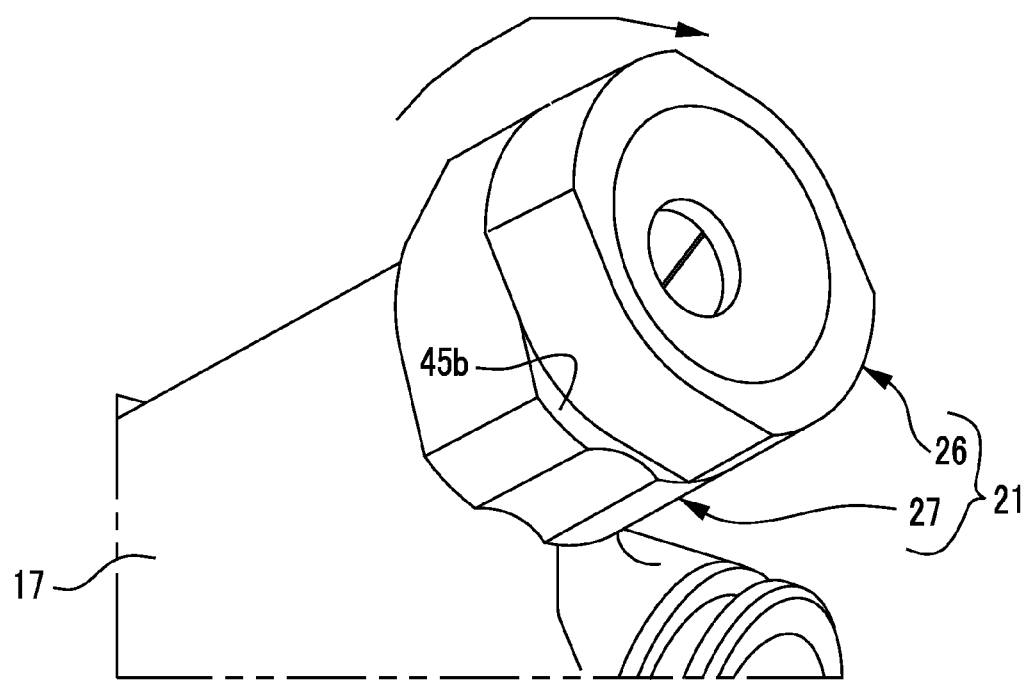
FIG. 14 is a perspective view of the forceps plug when the fixing member is set at the removal position.
Figure 15:
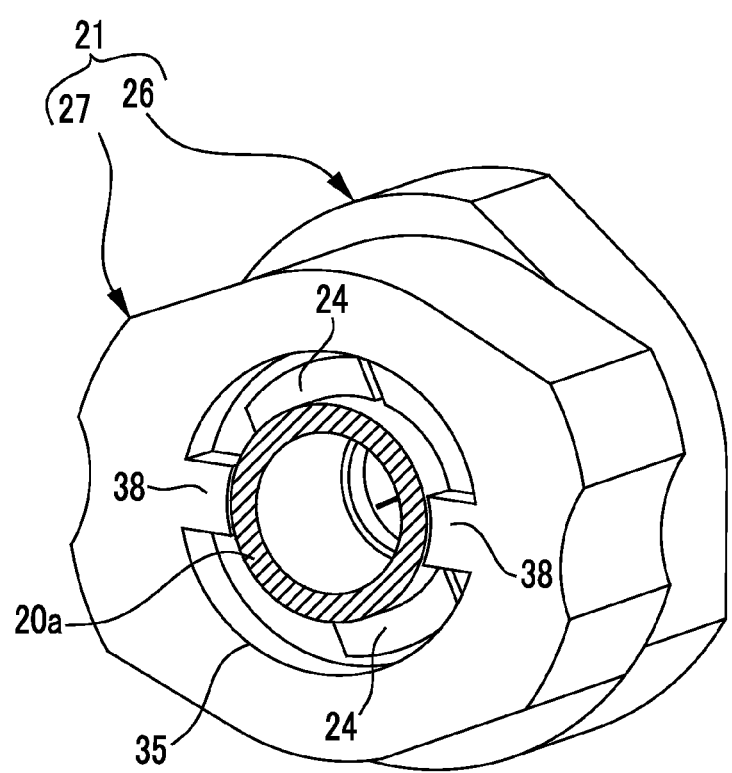
FIG. 15 is a perspective view of the forceps plug of FIG. 14 seen from the downward side.

As shown in FIG. 14, the fixing member 27 is rotated clockwise, and is set at the removal position from the fixed position. Thereby, as shown in FIG. 15, the engagement between the engaging claws 38 and the protrusions 24 is released to allow the removal of the forceps plug 21 from the opening 20. Next, the forceps plug 21 is removed from the opening 20 by manipulating to pull the forceps plug 21 upward.

Figure 16:
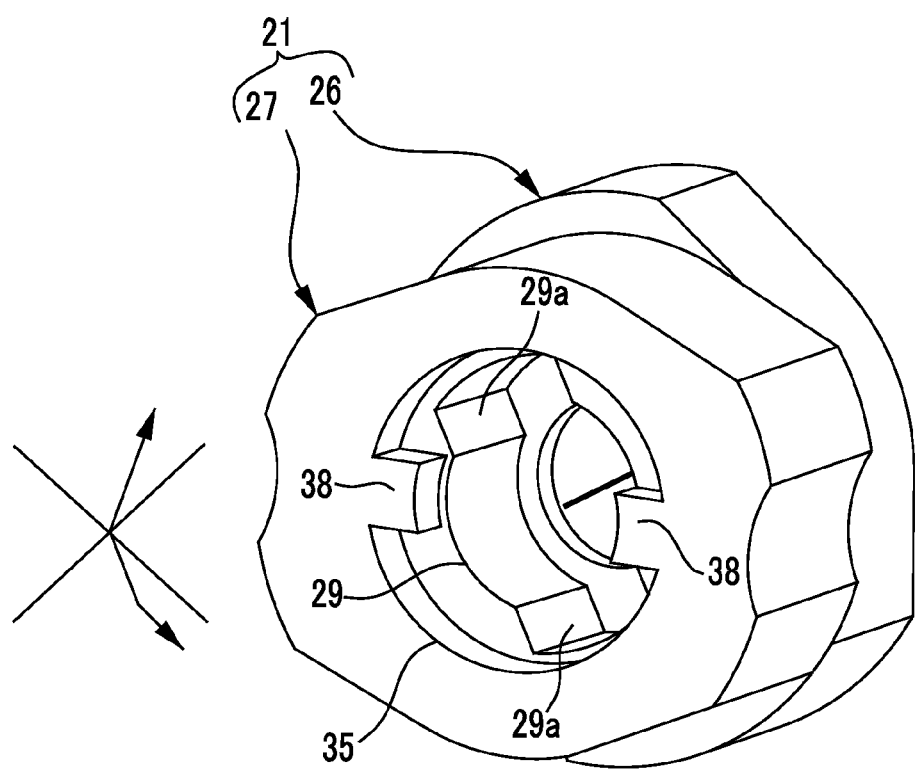
FIG. 16 is an explanatory view for explaining that reuse of the used forceps plug becomes impossible.

Additionally, when the fixing member 27 is set at the removal position, the ratchet claws 42 are locked to the rotation stop grooves 43. Thereby, as shown in FIG. 16, it becomes impossible to rotate the fixing member 27 clockwise and counterclockwise, the fixing member 27 cannot be again set at the fixed position. As a result, since it becomes impossible to fix the forceps plug 21 to the opening 20, reuse of the forceps plug 21 is prevented. Moreover, since the used mark 45b is exposed to the outside, it is possible to easily discriminate that the forceps plug 21 is a used plug.

Reuse of the forceps plug 21 can be prevented by providing the forceps plug 21 with the ratchet mechanism 40 without being accompanied by destruction of the forceps plug 21. Thereby, occurrence of troubles, such as entering of broken pieces produced by the destruction into the forceps channel 16 can be prevented. Additionally, since it becomes unnecessary to form a weakened part, such as a notch, a weakened part is no longer erroneously destroyed when the forceps plug 21 is attached to the opening 20.

[Second Embodiment]

Figure 17:
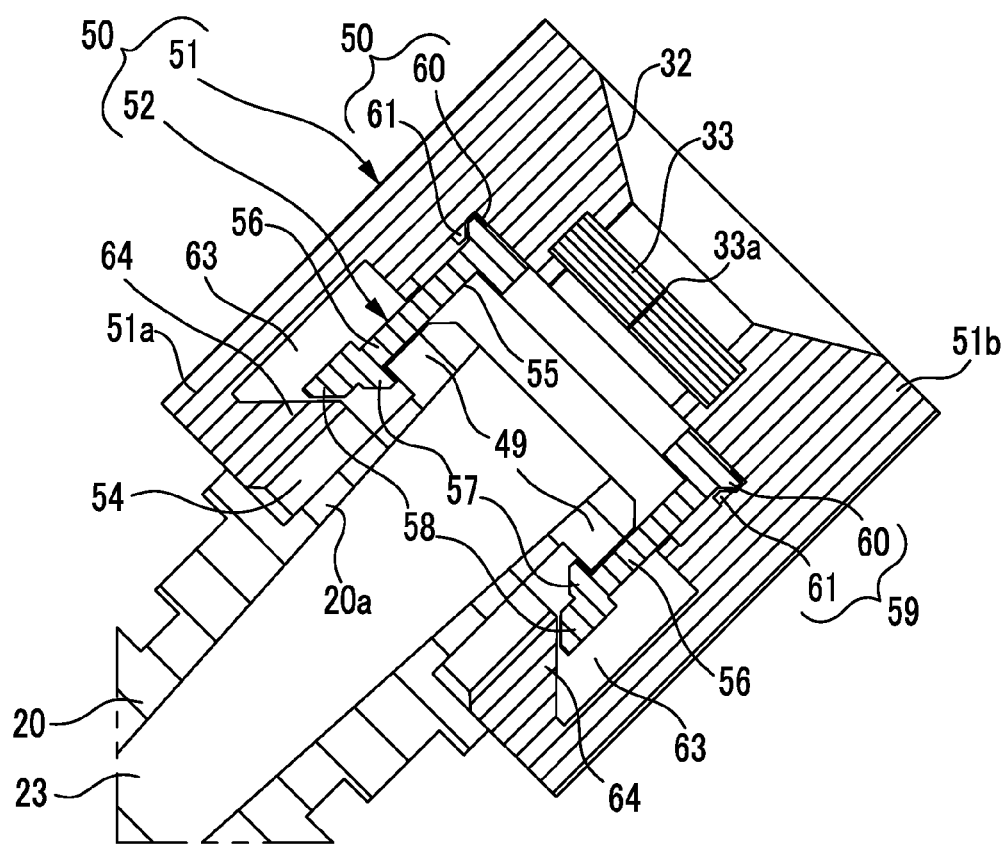
FIG. 17 is a cross-sectional view of an opening and a forceps plug of a second embodiment.
Figure 18:
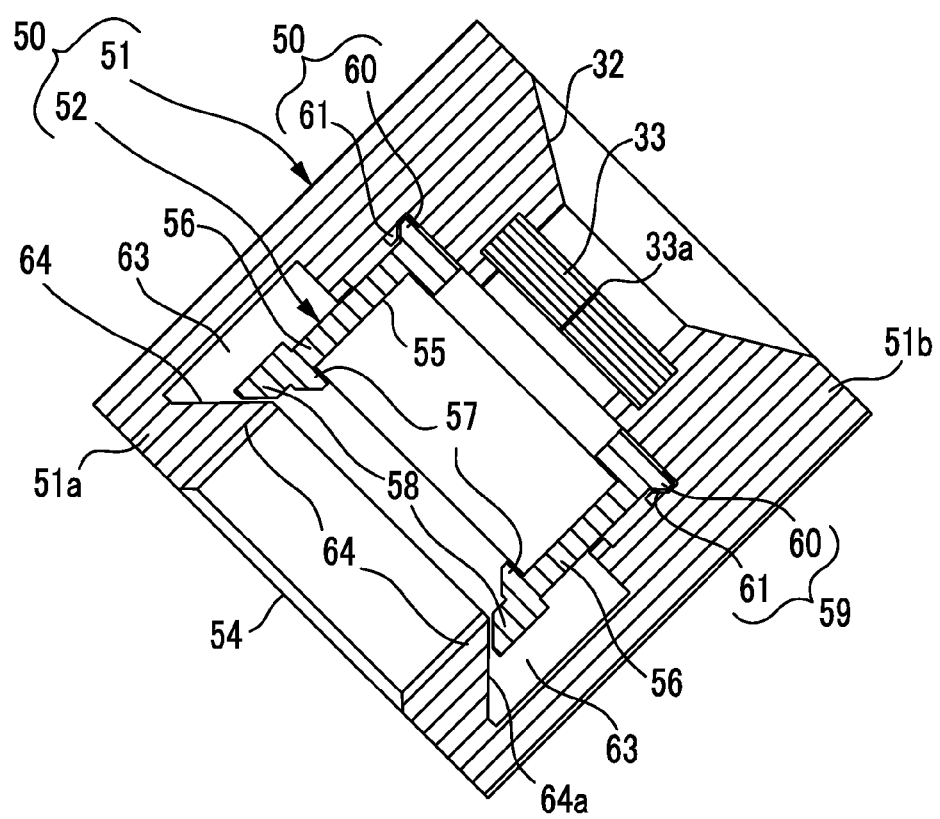
FIG. 18 is a cross-sectional view of the forceps plug of the second embodiment.
Figure 19:
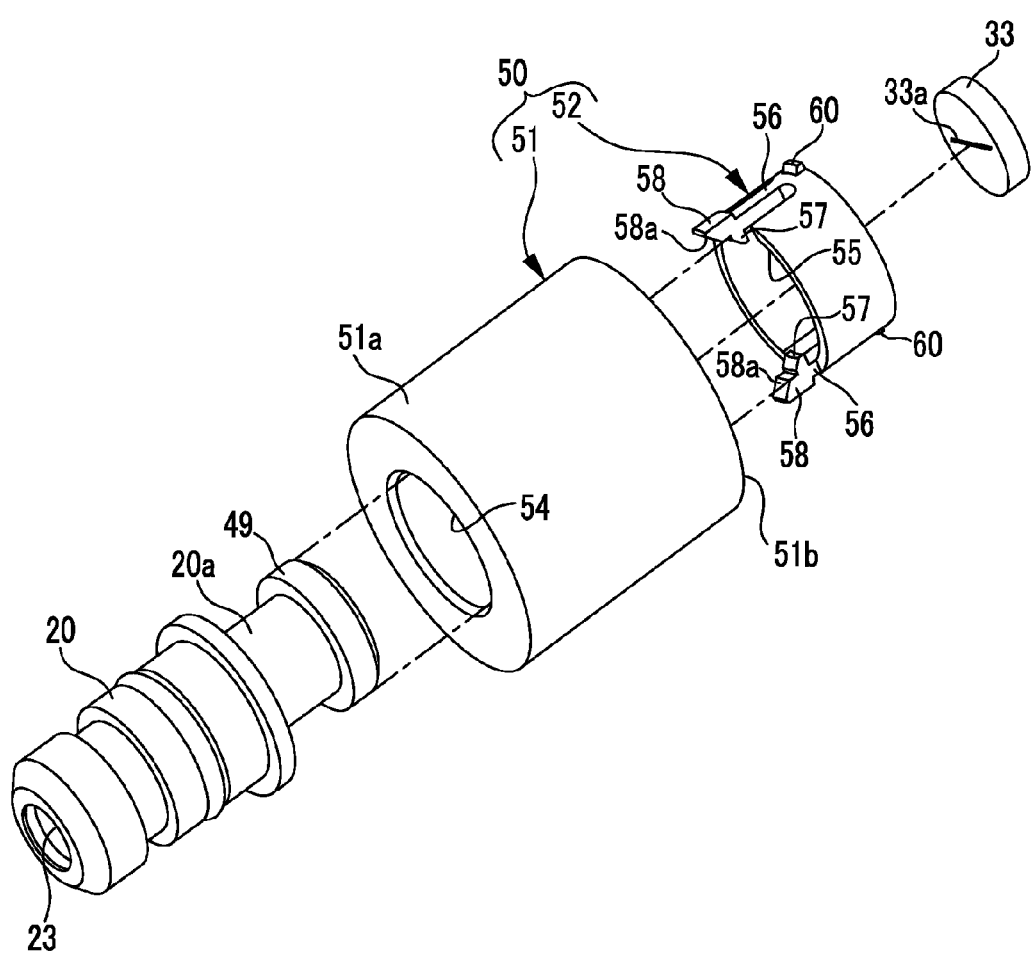
FIG. 19 is an exploded perspective view of the forceps plug of the second embodiment.

Next, an endoscope of a second embodiment of the present invention will be described with reference to FIGS. 17 to 19. Although the forceps plug 21 of the above first embodiment is provided with the rotary ratchet mechanism 40, a slide type ratchet mechanism is provided at the forceps plug in the second embodiment. In addition, the same components as the first embodiment in terms of functions and configuration are designated by the same reference numerals, and the description thereof is omitted.

The endoscope of the second embodiment fundamentally has the same configuration as the endoscope 10 of the first embodiment except that the flange 49 is formed at the tip of the opening tip portion 20a, and a forceps plug 50 different from the first embodiment is provided.

The forceps plug 50 is formed from resin materials, such as plastics, and includes a tubular plug main body 51 and a tubular fixing member 52 slidably held on the inner peripheral side of this plug main body 51.

The plug main body 51 includes a holding portion 51a that holds the fixing member 52 in a sliding movable manner in the opening axial direction, and a head 51b that has the treatment tool entrance 32 and the slit plate 33. The holding portion 51a has an outside insertion hole 54 into the opening tip portion 20a is inserted. The fixing member 52 is slidably held at the upper end portion of the outside insertion hole 54.

The fixing member 52 has an inside insertion hole 55 into which the opening tip portion 20a is inserted. A pair of arm portions 56 is formed at 180° to each other at the fixing member 52 by cutting out a portion of the fixing member. The arm portions 56 have a shape that extends long in the opening axial direction, and the lower end portions thereof become free end. The lower end portions of the arm portions 56 protrude downward beyond the lower end portion of the fixing member 52. Additionally, the lower end portion of each arm portion 56 is provided with an engaging claw 57 that protrudes toward the central axis of the fixing member 52 and an unfixing claw 58 that protrudes downward.

The engaging claw 57 covers a portion of an opening of the inside insertion hole 55, and engages the flange 49 of the opening tip portion 20a inserted into the inside insertion hole 55. The tip face of the unfixing claw 58 forms an inclined face 58a that inclines to the downward side gradually as being away from the central axis of the fixing member 52.

The inner peripheral surface of the holding portion 51a and the outer peripheral surface of the fixing member 52 is provided with a slide type ratchet mechanism 59. The ratchet mechanism 59 includes ratchet claws 60 formed on the outer peripheral surface of the fixing member 52, and ratchet gear teeth 61 formed on the inner peripheral surface of the holding portion 51a. The ratchet claws 60 are formed at 180° to each other at the upper end portion of the outer peripheral surface of the fixing member 52.

The ratchet gear teeth 61 are formed at 180° to each other at the upper end portion of the inner peripheral surface of the holding portion 51a. The ratchet gear teeth 61 engage the ratchet claws 60 to maintain a state where the upper end face of the fixing member 52 abuts on the head 51b. Additionally, the ratchet gear teeth 61 allow the ratchet claws 60 to ride thereover to the downward side, but stop the ratchet claws 60 that have ridden over the ratchet gear teeth 61 from returning to their original positions.

Such a ratchet mechanism 59 allows the fixing member 52 to move in order of the following fixed position and removal position, but stops movement of the fixing member 52 once moved to the removal position, to the fixed position.

The fixed position is a position where the ratchet claws 60 engage the ratchet gear teeth 61. In addition, in the fixed position of the second embodiment, attachment of the forceps plug 50 to the opening 20 is also performed. Additionally, the removal position is a position where the ratchet claws 60 have moved to the downward side of the ratchet gear teeth 61 (refer to FIG. 20).

Recesses 63 are formed at positions that face the arm portions 56 in the inner peripheral surface of the holding portion 51*a*. Additionally, an unfixing claw 64 (unfixing portion) that protrudes toward the unfixing claw 58 is formed in the wall face of each recess 63 on the downward side. The tip face of the unfixing claw 64 becomes an inclined face 64*a* that becomes substantially parallel to an inclined face 58*a*. The inclined face 64*a* is close to the unfixing claw 58 of the fixing member 52 at the fixed position.

Next, the attachment and removal processing of the forceps plug 50 of the above configuration will be described. In addition, the fixing member 52 is set at the fixed position in the stage of the shipment from a maker.

First, positioning of the forceps plug 50 is performed so that the center of the outside insertion hole 54 and the center of the inside insertion hole 55 coincide with the center of the opening tip portion 20*a*. Next the forceps plug 50 is pressed against the opening tip portion 20*a*. Thereby, the engaging claws 57 are pressed by the flange 49, and the arm portions 56 are curved in the shape of a circular arc in a direction away from the outer peripheral surface of the opening tip portion 20*a*. Then, the pressing manipulation is continued until the flange 49 rides over the engaging claws 57.

If the flange 49 rides over the engaging claws 57, the arm portions 56 restore to their original shape. Thereby, the engaging claws 57 engage the flange 49. The forceps plug 50 is fixed to the opening 20 in this way. The attachment processing of the forceps plug 50 is completed above. Then, after the endoscopic examination and treatment are completed, the removal processing of the forceps plug 50 is started.

Figure 20:
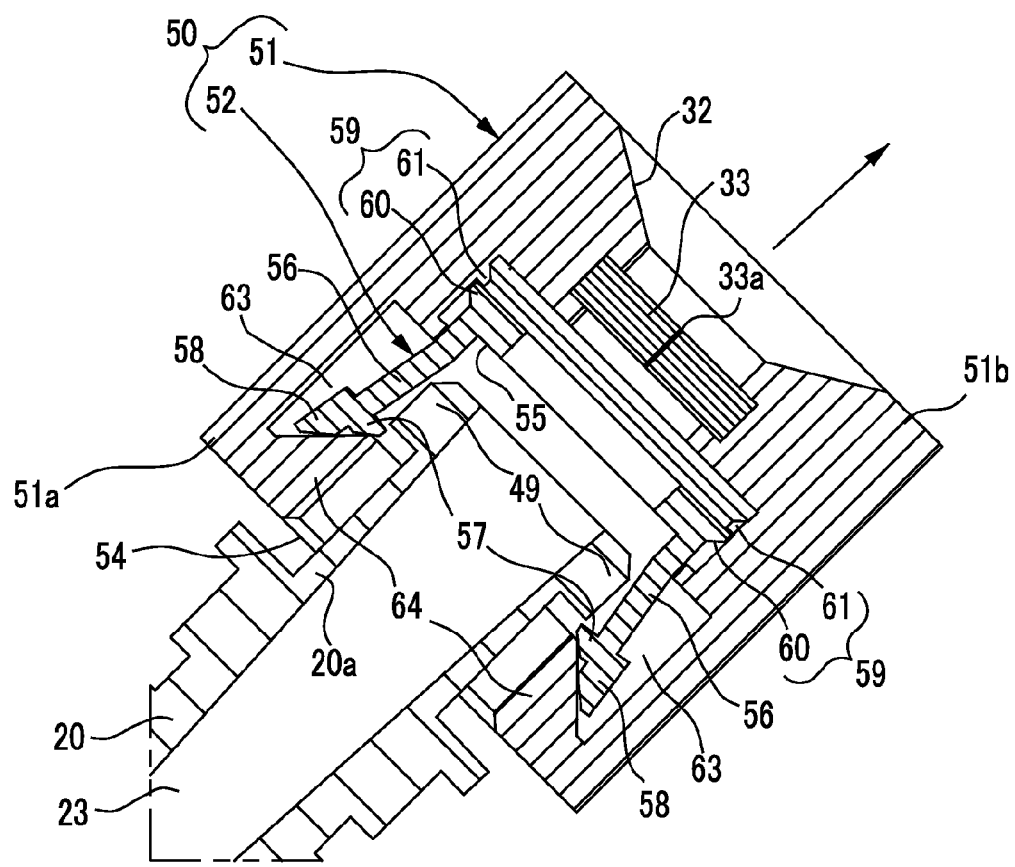
FIG. 20 is a cross-sectional view of the forceps plug of the second embodiment, showing a state when a fixing member has moved to a removal position relative to a plug main body.

Since the engagement between the flange 49 and the engaging claws 57 is maintained if pulling manipulation of the plug main body 51 is performed, the ratchet claws 60 ride over the ratchet gear teeth 61 and move to the downward side after the engagement between the ratchet claws 60 and the ratchet gear teeth 61 is released. Thereby, as shown in FIG. 20, the fixing member 52 moves the removal position relative to the plug main body 51.

As the fixing member 52 moves to the removal position, the inclined faces 64*a* of the unfixing claws 64 are brought into pressure contact with the inclined faces 58*a* of the unfixing claws 58. Thereby, the arm portions 56 are curved in the shape of a circular arc away from the outer peripheral surface of the opening tip portion 20*a*, whereby the engagement between the engaging claws 57 and the flange 49 is released. In this way, the removal of the forceps plug 50 from the opening 20 is allowed. By continuing the pulling manipulation, the forceps plug 50 is removed from the opening 20.

Figure 21:
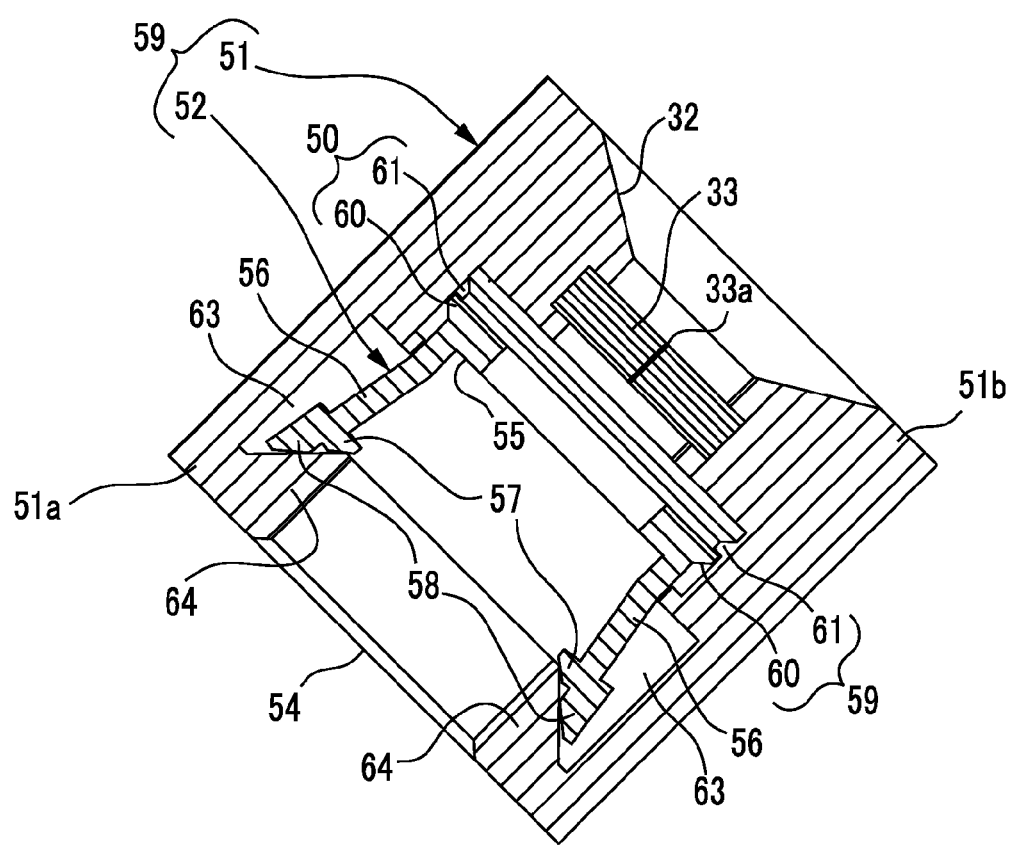
FIG. 21 is an explanatory view for explaining that reuse of the used forceps plug of the second embodiment becomes impossible.

As shown in FIG. 21, the movement of the fixing member 52 of the forceps plug 50 to the fixed position is regulated by the ratchet gear teeth 61. As a result, since it becomes impossible to fix the forceps plug 50 to the opening 20, reuse of the forceps plug 50 is prevented. Thereby, the same effects as the first embodiment are obtained.

[Third Embodiment]

Figure 22:
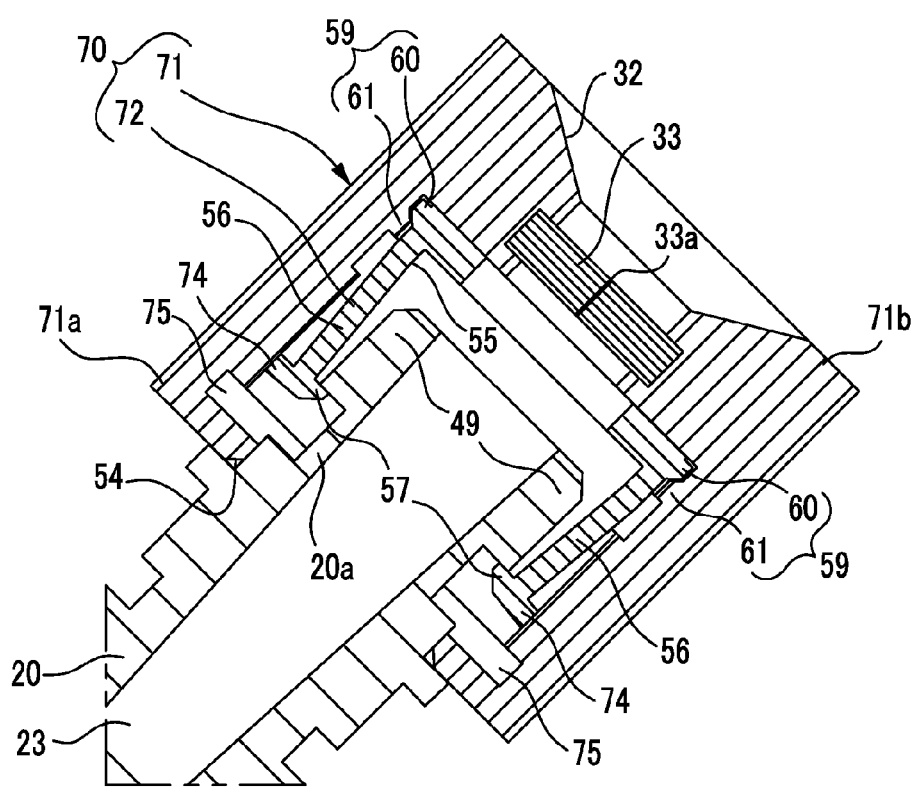
FIG. 22 is a cross-sectional view of an opening and a forceps plug of a third embodiment.
Figure 23:
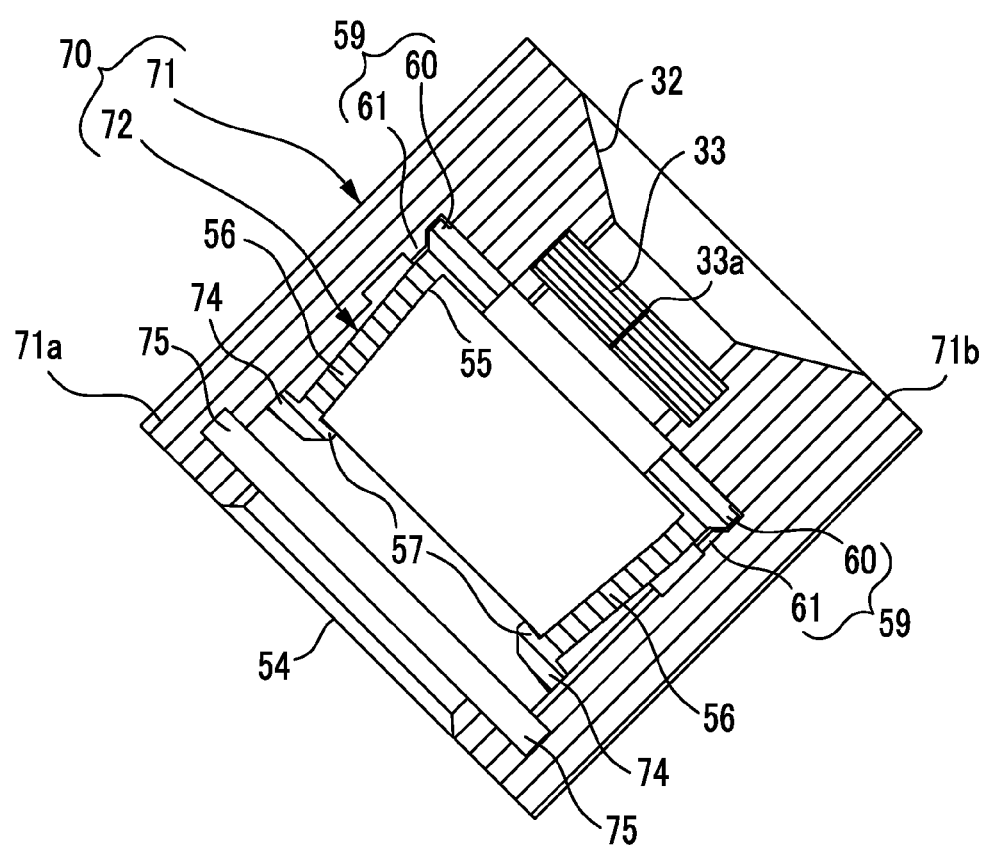
FIG. 23 is a cross-sectional view of the forceps plug of the third embodiment.
Figure 24:
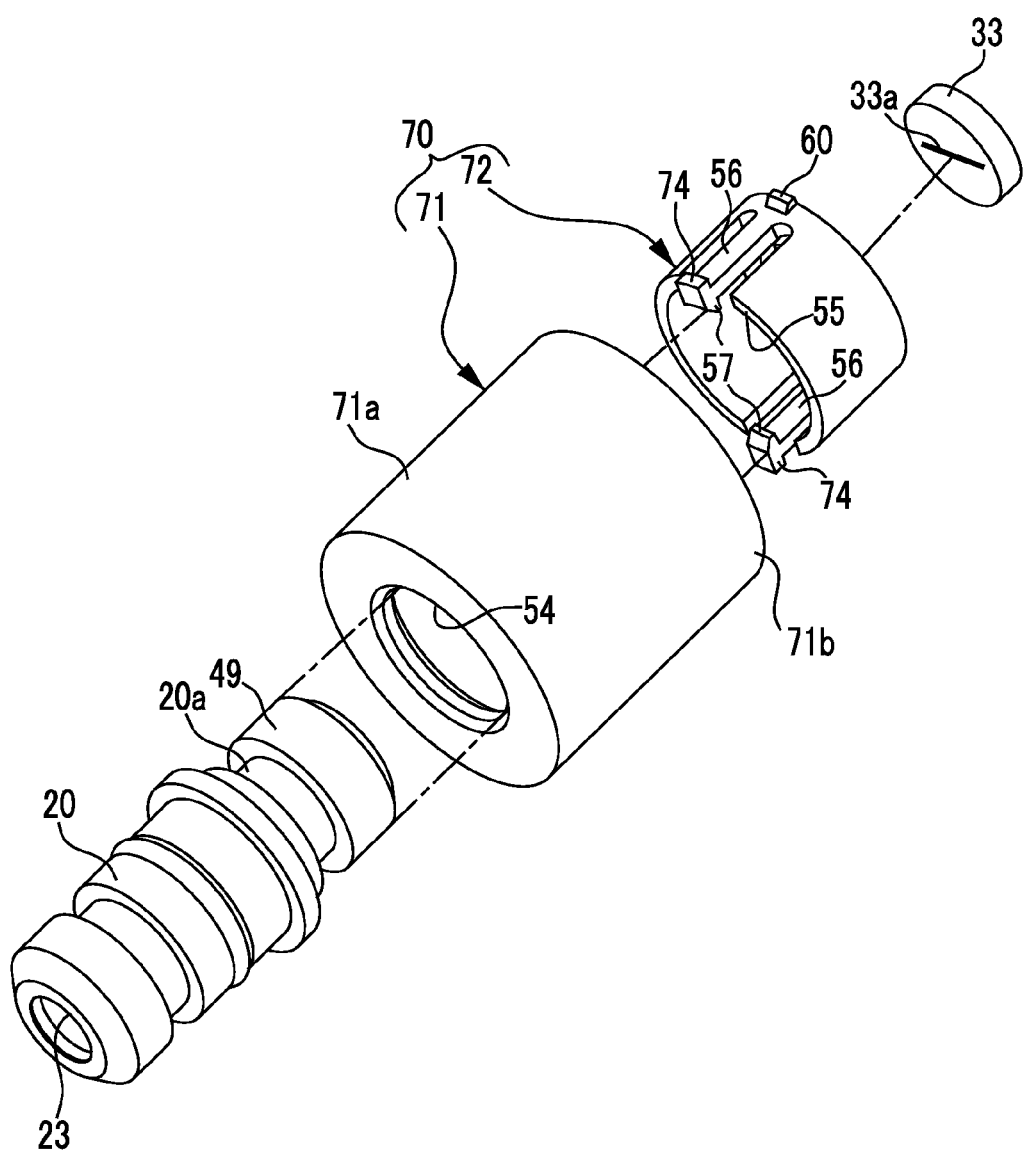
FIG. 24 is an exploded perspective view of the forceps plug of the third embodiment.

Next, an endoscope of a third embodiment of the present invention will be described with reference to FIGS. 22 to 24. In the forceps plug 50 of the above second embodiment, unfixing claws 64 release the engagement between the engaging claws 57 and the flange 49. However, in the third embodiment, the engagement between both is released using the restoring force of the arm portions. In addition, since the third embodiment fundamentally has the same configuration as the second embodiment, the same components as those of the second embodiment in terms of functions and configuration are designated by the same reference numerals, and the description thereof is omitted.

A forceps plug 70 includes a tubular plug main body 71, a tubular fixing member 72 slidably held on the inner peripheral side of the plug main body 71, and the ratchet mechanism 59. The plug main body 71 includes a holding portion 71*a* that slidably holds the fixing member 72 in the opening axial direction, and a head 71*b* that has the treatment tool entrance 32 and the slit plate 33.

The fixing member 72 fundamentally has the same configuration as the fixing member 52 of the second embodiment except that protruding portions 74 are provided at the lower end portions of the arm portions 56 instead of the unfixing claws 58. The protruding portions 74 protrude toward the inner peripheral surface of the holding portion 71*a*. The protruding portions 74 are formed so as to be sufficiently longer the distance between the inner peripheral surface of the holding portion 71*a*, and the arm portions 56 in a natural state. Thereby, the protruding portions 74 receives the pressing from the inner peripheral surface of the holding portion 71*a*, and deflect the arm portions 56 substantially in the shape of a circular arc toward the opening tip portion 20*a*. As a result, the engaging claws 57 can be maintained in a state where the engaging claws are engaged with the flange 49.

Similarly the second embodiment, the ratchet mechanism 59 allows the fixing member 72 to move in order of the following fixed position and removal position, but stops movement of the fixing member 72 moved to the removal position, to the fixed position.

The holding portion 71*a* fundamentally has the same configuration as the holding portion 51*a* of the first embodiment. However, fitting grooves 75 to which the protruding portions 74 fit are formed in the inner peripheral surface of the holding portion 71*a* instead of the recesses 63 and the unfixing claws 64. The fitting grooves 75 are formed at positions where the protruding portions 74 fit when the fixing member 72 has moved to the removal position relative to the holding portion 71*a*.

Next, the attachment and removal processing of the forceps plug 70 of the above configuration will be described. In addition, the attachment processing of the forceps plug 70 is fundamentally the same as that of the second embodiment. However, since the protruding portions 74 abut on the inner peripheral surface of the holding portion 71*a*, attachment of the forceps plug 70 is allowed as the engaging claws 57 are pressed and elastically deformed by the flange 49 at the time of the pressing manipulation of the forceps plug 70. Then, after the endoscopic examination and treatment are completed, the removal processing of the forceps plug 70 is started.

Figure 25:
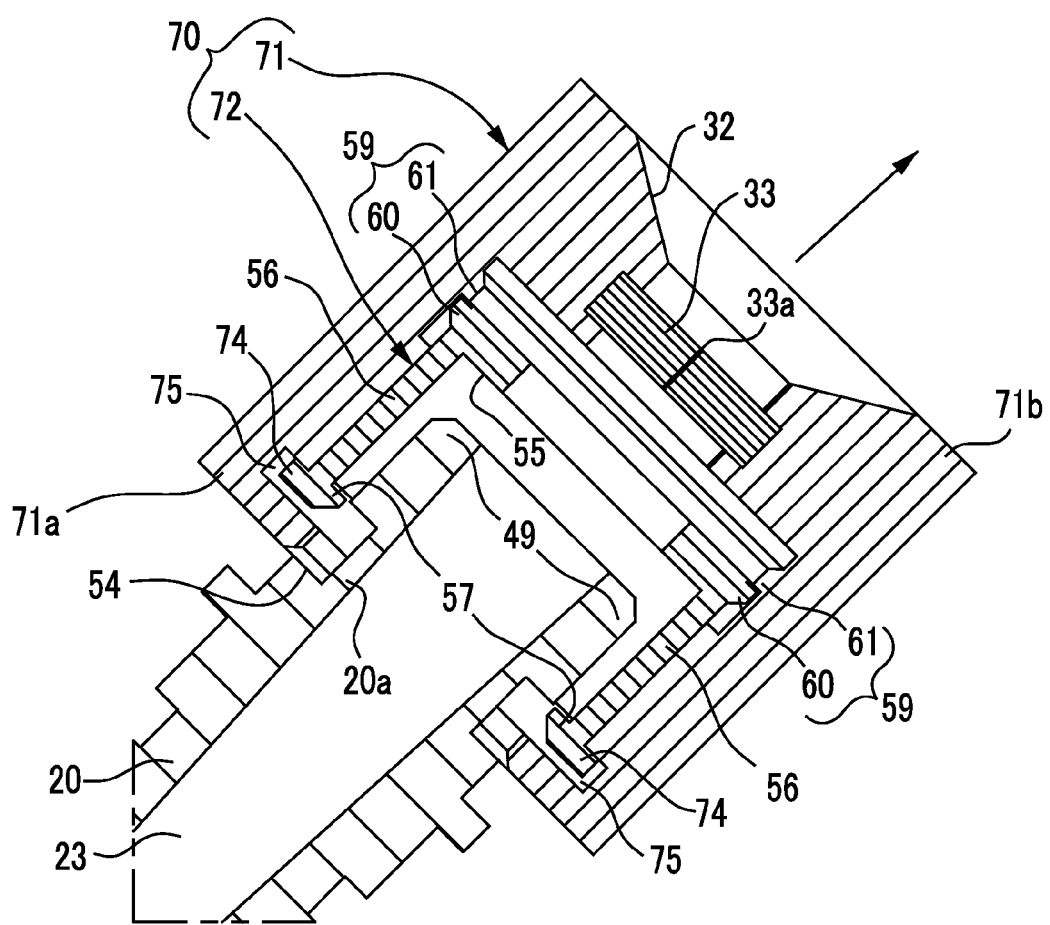
FIG. 25 is a cross-sectional view of the forceps plug of the third embodiment, showing a state when a fixing member has moved to a removal position relative to a plug main body.

If the pulling manipulation of the plug main body 71 is performed as shown in FIG. 25, the fixing member 72 moves to the removal position relative to the plug main body 71 by the engagement between the flange 49 and the engaging claws 57. Thereby, as the protruding portions 74 fit into the fitting grooves 75 and the arm portions 56 restore to their original shape, the engagement between the flange 49 and the engaging claws 57 is released. By continuing the pulling manipulation, the forceps plug 70 is removed from the opening 20.

Figure 26:
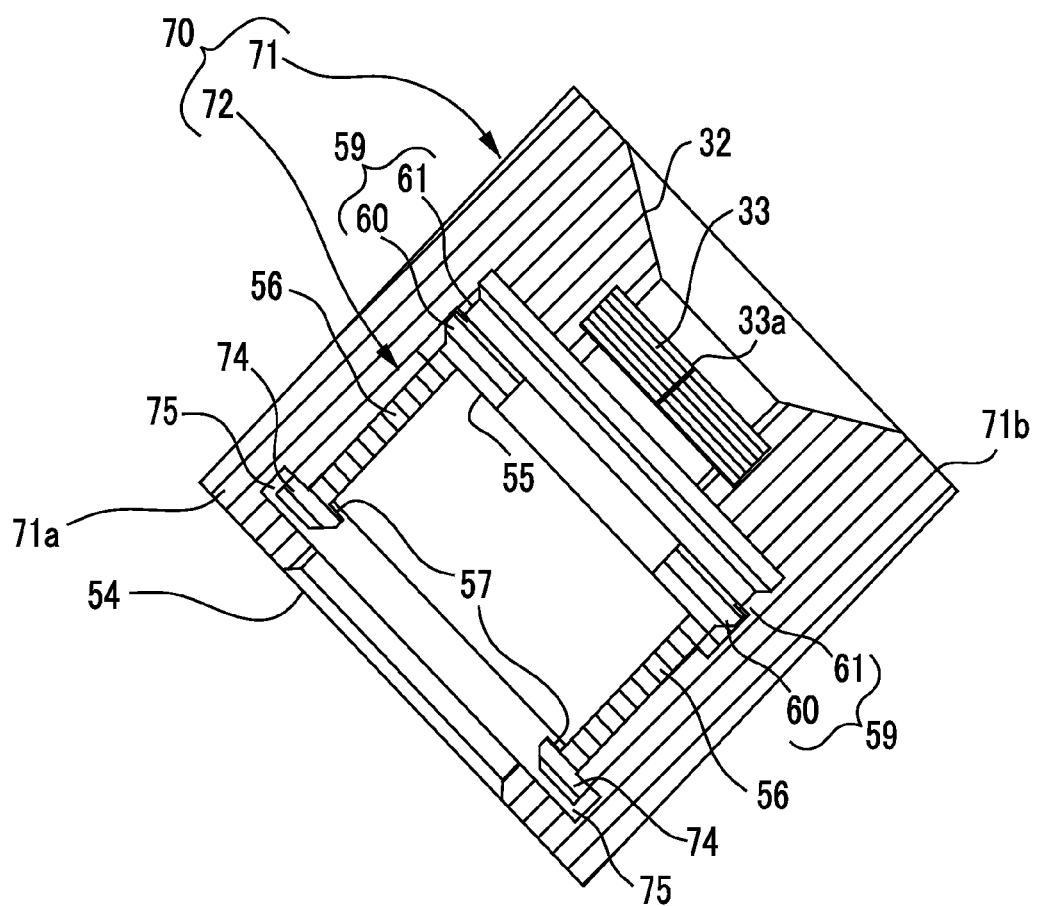
FIG. 26 is an explanatory view for explaining that reuse of the used forceps plug of the third embodiment becomes impossible.

As shown in FIG. 26, since the movement of the fixing member 72 of the forceps plug 70 to the fixed position is regulated by the ratchet gear teeth 59, reuse of the forceps plug 70 is prevented similarly to the second embodiment. Thereby, the same effects as the first embodiment are obtained.

[Fourth Embodiment]

Figure 27:
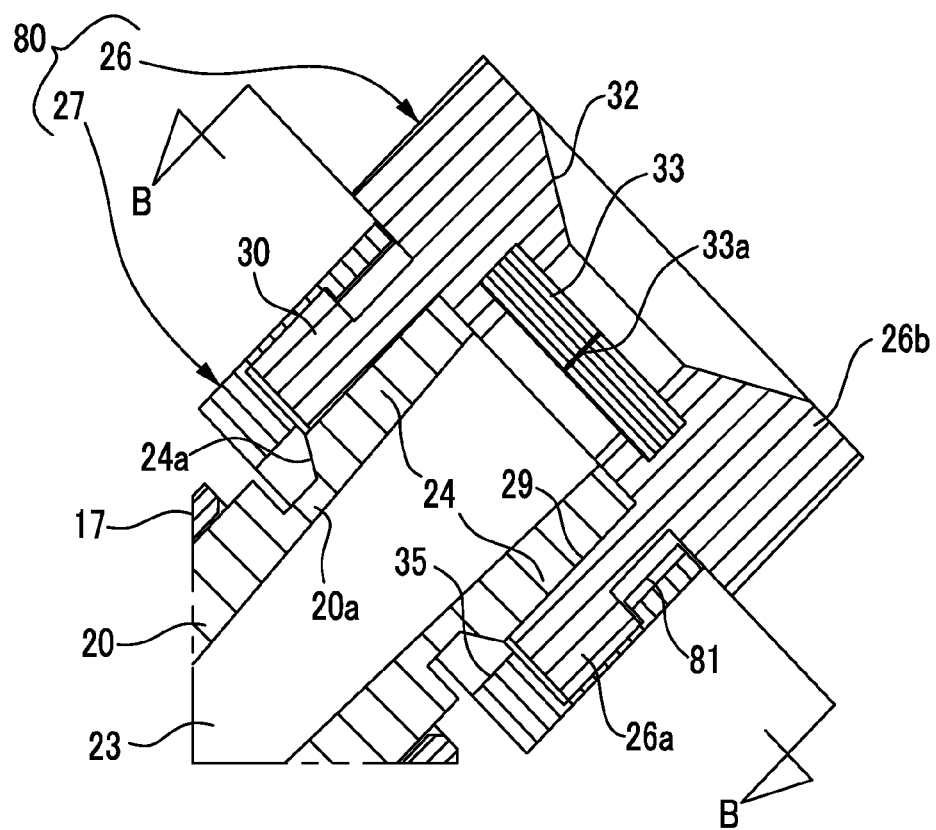
FIG. 27 is a cross-sectional view of a forceps plug of a fourth embodiment.
Figure 28:
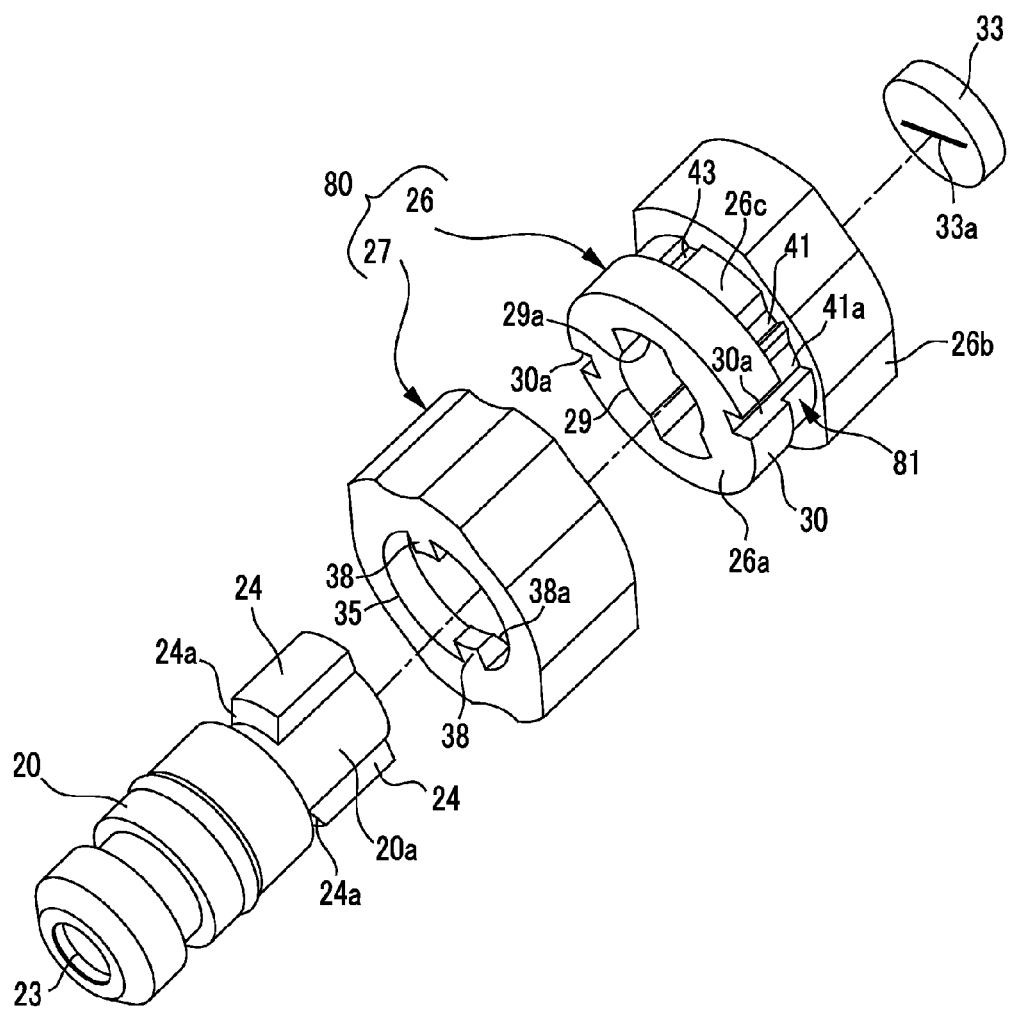
FIG. 28 is an exploded perspective view of the forceps plug of the fourth embodiment.

Next, an endoscope of a fourth embodiment of the present invention will be described with reference to FIGS. 27 to 29. In the above first embodiment, reuse of the forceps plug 21 is prevented by not allowing the used forceps plug 21 to be fixed to opening 20. In contrast, in the fourth embodiment, reuse of the forceps plug is prevented by stopping the attachment of a used forceps plug to the opening 20.

The endoscope of the fourth embodiment fundamentally has the same configuration as the endoscope 10 of the first embodiment except that the lower end faces of the protrusions 24 become inclined faces 24a that incline to the upward side gradually as being away from the central axis of the opening 20, and a different forceps plug 80 different from the first embodiment is provided. In addition, the same components as the first embodiment in terms of functions and configuration are designated by the same reference numerals, and the description thereof is omitted.

The forceps plug 80 includes the plug main body 26 and the fixing member 27, and a ratchet mechanism 81 different from the first embodiment. However, the upper end faces of the engaging claws 38 becomes inclined faces 38a substantially parallel to the inclined faces 24a.

The ratchet mechanism 81 includes the ratchet grooves 41 formed in the outer peripheral surface upper end portion 26c, the pair of incorporating ratchet grooves 41a, the pair of rotation stop grooves 43, and the pair of ratchet claws 42 formed on the inner peripheral surface of the fixing member 27. Additionally, in the ratchet mechanism 81, when the ratchet claws 42 engage the rotation stop grooves 43, the position of the rotation stop grooves 43 is changed so that the engaging claws 38 cover portions of the openings of the protrusion insertion holes 29a. Moreover, one ratchet groove 41 is formed between the incorporating ratchet groove 41a and the rotation stop groove 43.

Such a ratchet mechanism 81 allows the fixing member 27 to rotate in the clockwise direction, to move to a total of following three positions, that is, an incorporation position, an attachment position, and a fixed position in order, but stops further movement to a position where the fixing member has moved once.

Figure 29:
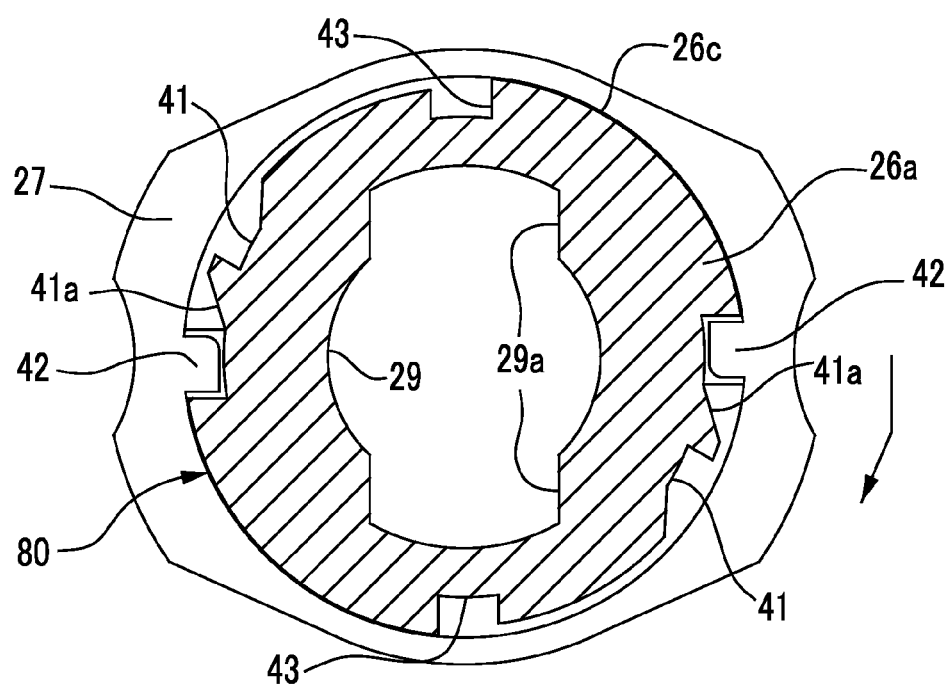
FIG. 29 is a cross-sectional view along line B-B in FIG. 27, showing a state where a fixing member is set in its incorporated location.
Figure 30:
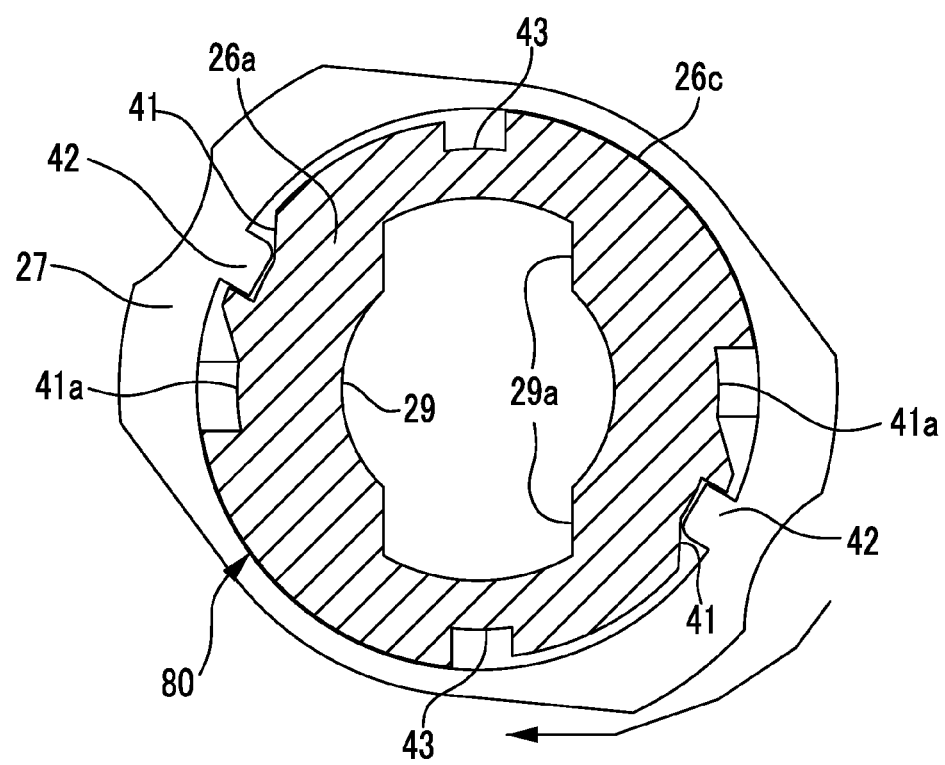
FIG. 30 is a cross-sectional view along line B-B in FIG. 27, showing a state where the fixing member is set at an attachment position.

As shown in FIG. 29, similarly to the first embodiment, the incorporation position is a position where the ratchet claws 42 engage the incorporating ratchet grooves 41a. As shown in FIG. 30, the attachment position is a position where the ratchet claws 42 engage the ratchet grooves 41, and is a position set when the forceps plug 80 is attached to the opening tip portion 20a.

Figure 31:
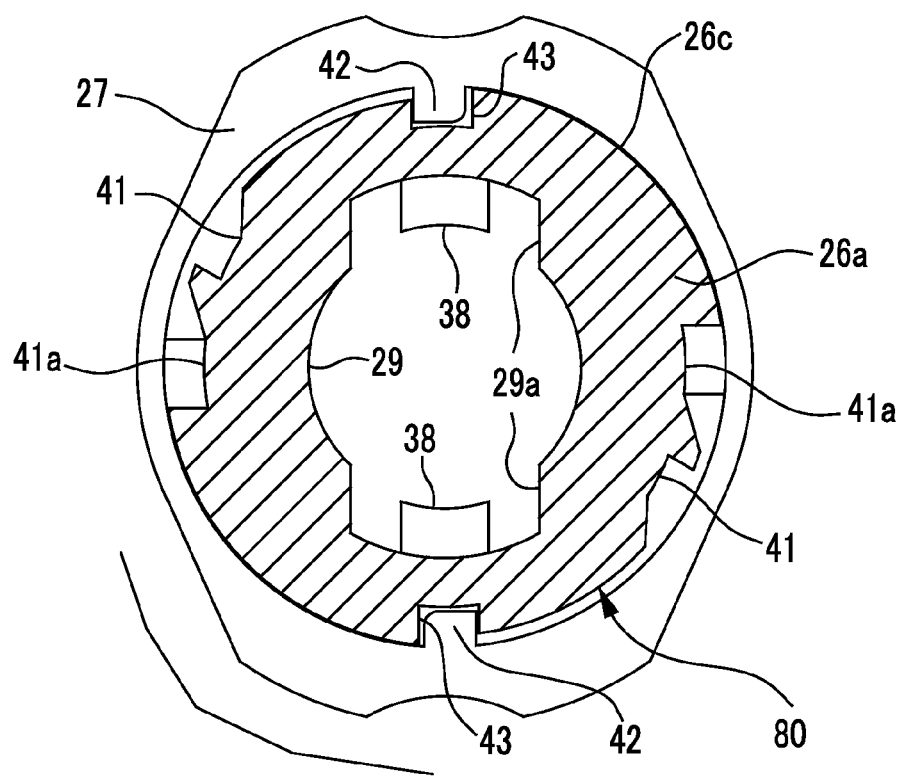
FIG. 31 is a cross-sectional view along line B-B in FIG. 27, showing a state where the fixing member is set at a fixed position.

As shown in FIG. 31, the fixed position is a position where the ratchet claws 42 engage the rotation stop grooves 43. The fixed position is a position set when the forceps plug 80 is fixed to the opening tip portion 20a, and the engaging claws 38 cover portions of the protrusion insertion holes 29a at this position.

Next, the attachment and removal processing of the forceps plug 80 of the above configuration will be described. In addition, since the attachment processing of the forceps plug 80 is fundamentally the same as the first embodiment, the specific description thereof is omitted herein. However, since the ratchet claws 42 are locked to the rotation stop grooves 43 when the fixing member 27 is set at the fixed position, the fixing member 27 cannot be rotated in any direction of the clockwise direction and the counterclockwise direction. Then, after the endoscopic examination and treatment are completed, the removal processing of the forceps plug 80 is started.

Figure 32:
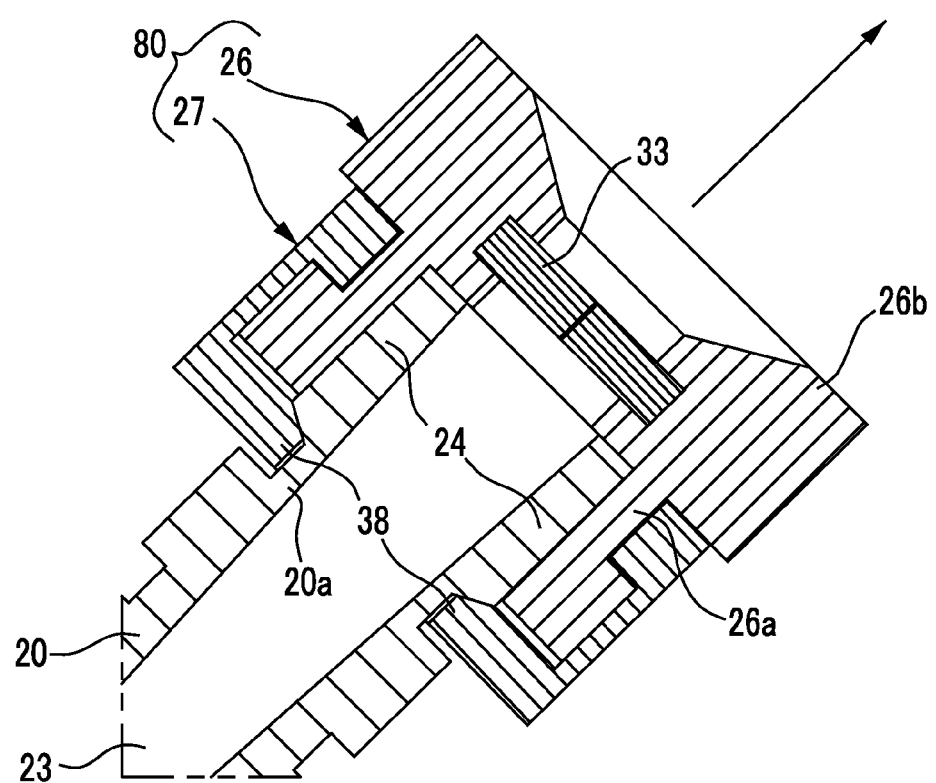
FIG. 32 is an explanatory view for explaining removal processing of the forceps plug of the fourth embodiment from the opening.

As shown in FIG. 32, if the pulling manipulation of the plug main body 26 is performed, the inclined faces 38a of the engaging claws 38 are pressed against the inclined faces 24a of the protrusions 24, and the engaging claws 38 are deflected downward in the shape of a circular arc. If the pulling manipulation is continued against the elastic force of the engaging claws 38, the amount of deflection of the engaging claws 38 increases gradually. If the amount of deflection of the engaging claws 38 exceeds a certain value, the engagement between the engaging claws 38 and the protrusions 24 is released, and the forceps plug 80 is removed from the opening 20.

Figure 33:
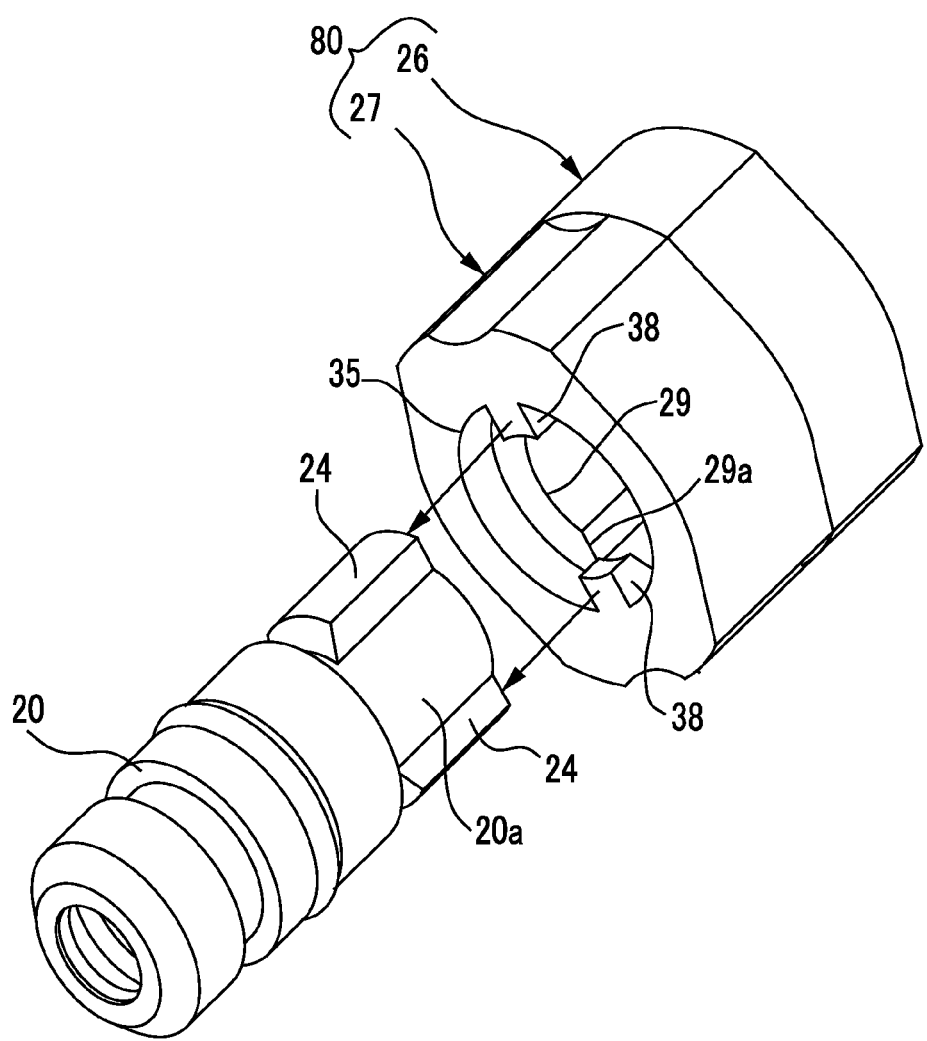
FIG. 33 is an explanatory view for explaining that reuse of the used forceps plug of the fourth embodiment becomes impossible.
Figure 34:
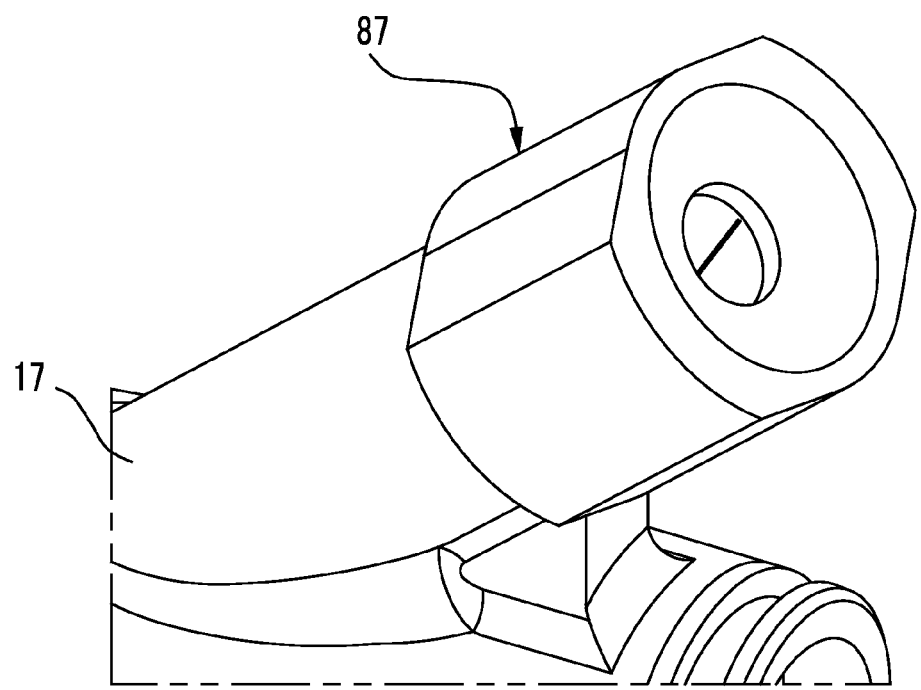
FIG. 34 is a perspective view of a forceps plug of a fifth embodiment.
Figure 35:
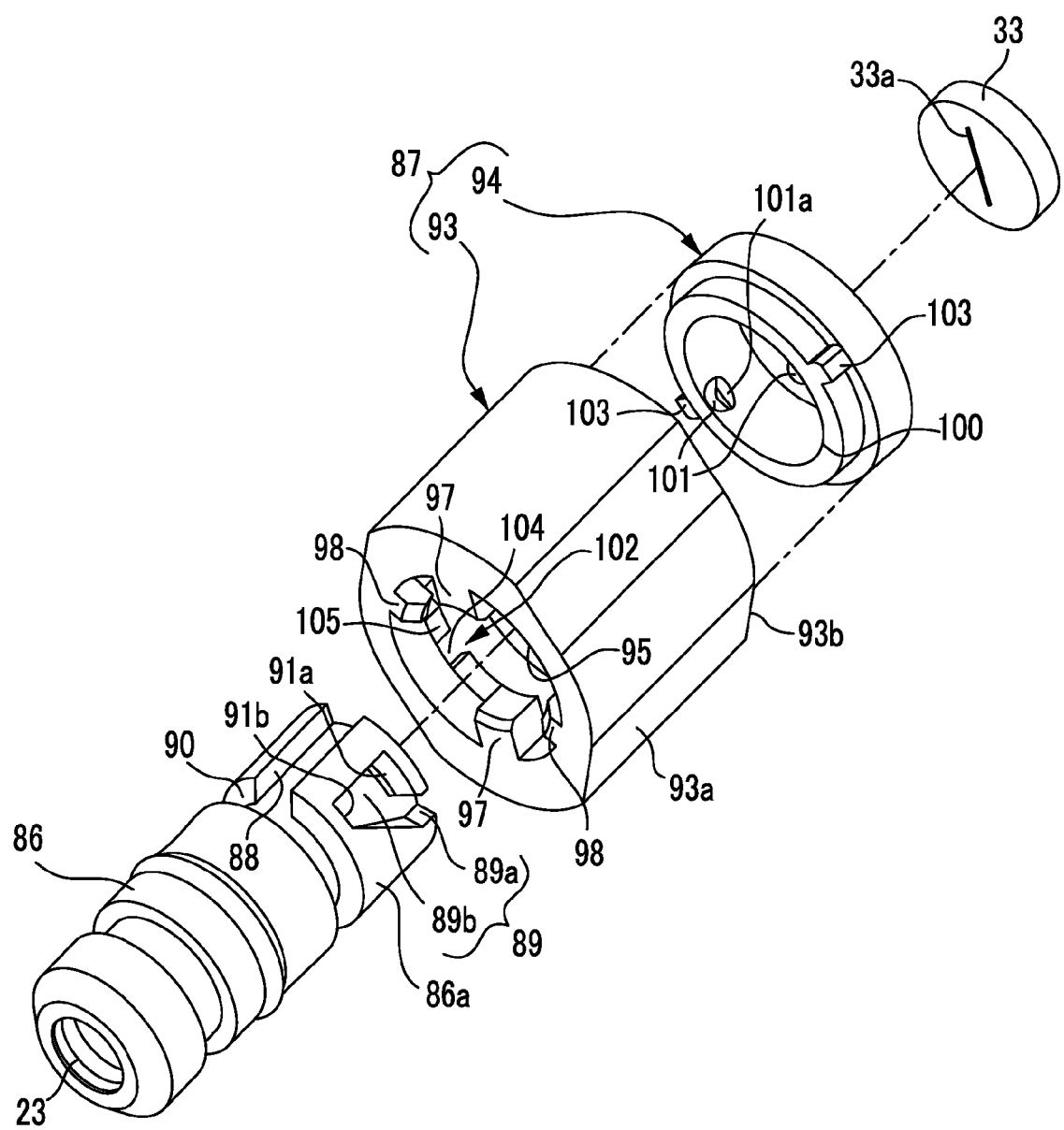
FIG. 35 is an exploded perspective view of the forceps plug of the fifth embodiment.
Figure 36:
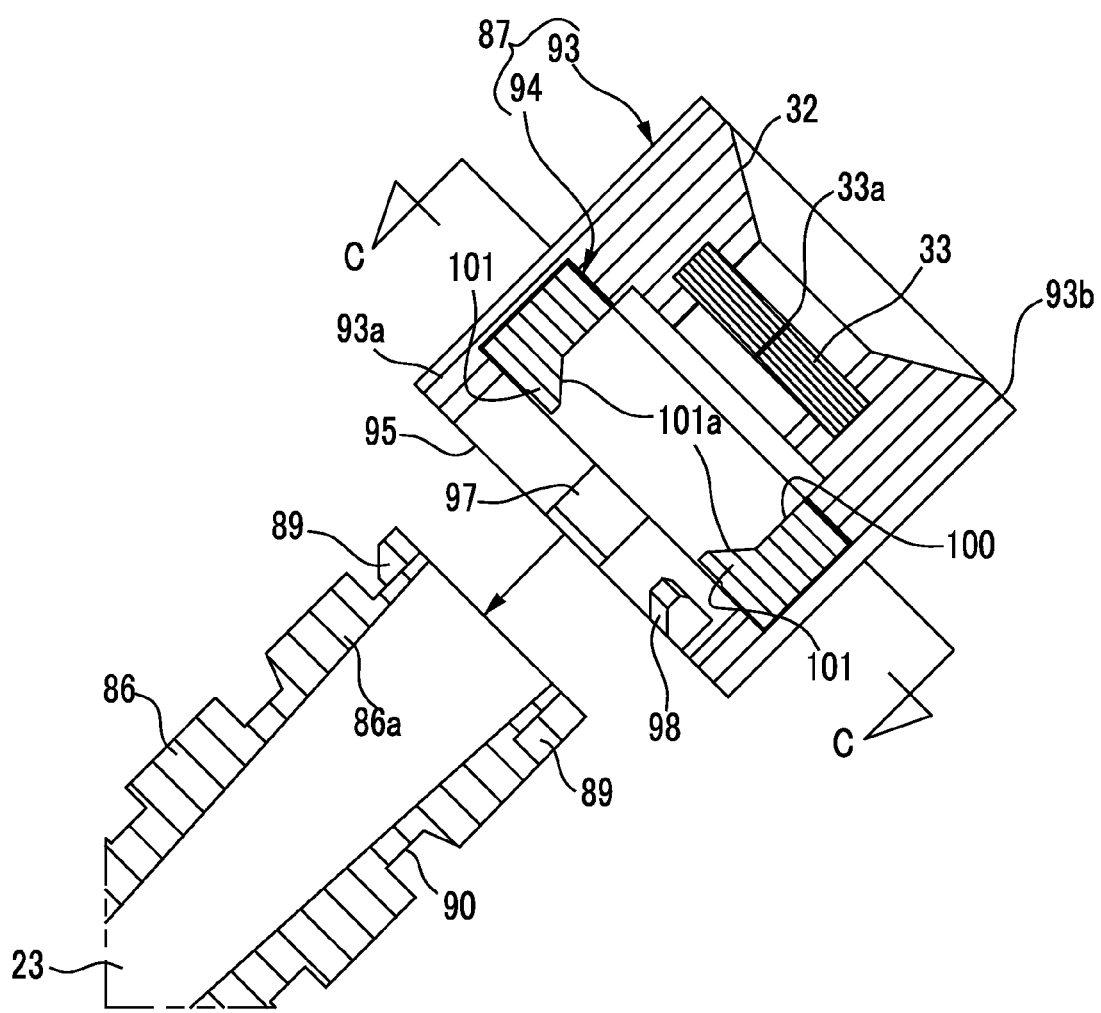
FIG. 36 is a cross-sectional view of the forceps plug of the fifth embodiment.
Figure 37:
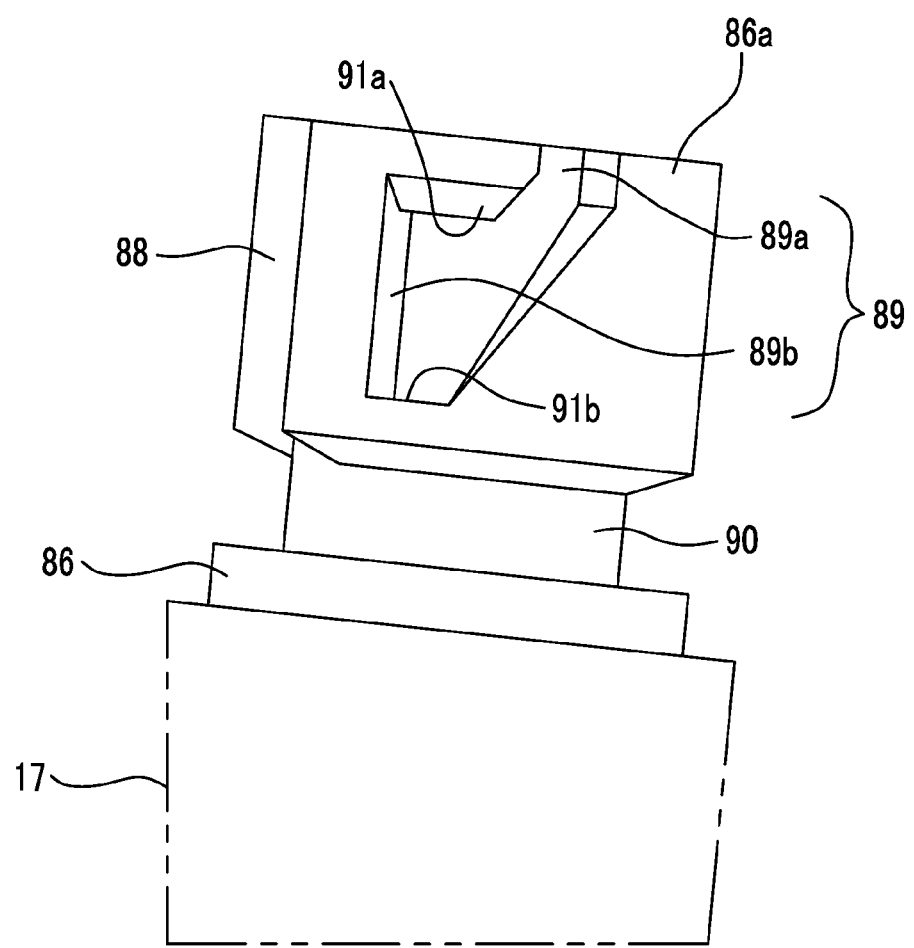
FIG. 37 is a perspective view of the opening.

Since the fixing member 27 of the forceps plug 80 removed from the opening 20 is locked at the fixed position as shown in FIG. 33, portions of the openings of the protrusion insertion holes 29a remain covered with the engaging claws 38. For this reason, since the protrusions 24 interferes with the engaging claws 38 when the opening tip portion 20a is inserted into the inside insertion hole 29, the opening tip portion 20a cannot be advanced to the inner part of the inside insertion hole 29. As a result, since the forceps plug 80 cannot be attached to the opening 20, reuse of the forceps plug 80 is prevented. Thereby, the same effects as the first embodiment are obtained.

[Fifth Embodiment]

Next, an endoscope of a fifth embodiment of the present invention will be described with reference to FIGS. 34 to 37. In the above fourth embodiment, the fixing member 27 is set at the fixed position from the attachment position by manual operation. In contrast, in the fifth embodiment, the fixing member is automatically set at the fixed position when the forceps plug is attached to the opening.

The endoscope of the fifth embodiment fundamentally has the same configuration as the fourth embodiment except that an opening 86 and a forceps plug 87 different from the fourth embodiment are provided. The same components as those of the above fourth embodiment in terms of functions and structure are designated by the same reference numerals, and the description thereof is omitted.

The opening 86 has an opening tip portion 86a different from the fourth embodiment. A pair of rails 88 and a pair of cam grooves 89 are alternately formed at pitches of 90° in the outer peripheral surface of the opening tip portion 86a. Additionally, an annular groove 90 is formed in the rear end of the opening tip portion 86a.

The rails 88 have a shape that extends long so as to run along the opening axial direction toward the annular groove 90 from the tip of the opening tip portion 86a.

Each cam groove 89 includes a guide portion 89a and an engaged portion 89b. The guide portion 89a offsets in the clockwise direction beyond this tip, from the tip of the opening tip portion 86a, and extends in a substantially oblique direction to a position near the annular groove 90. The engaged portion 89b extends along the clockwise direction from the end point of the guide portion 89a. In both the wall faces that form the engaged portion 89b, a wall face on the upward side an inclined face 91a that inclines to the upward side gradually away from the central axis of the opening 86, and the wall face on the downward side becomes a vertical face 91*b*.

The forceps plug 87 includes a tubular plug main body 93, and a tubular fixing member 94 rotatably held free on the inner peripheral side of the plug main body 93. The plug main body 93 includes a holding portion 93*a* that rotatably holds the fixing member 94, and a head 93*b* that has the treatment tool entrance 32 and the slit plate 33.

The holding portion 93*a* has an outside insertion hole 95 into which the opening tip portion 86*a* is inserted. An inner surface that forms the opening of the outside insertion hole 95 is formed with a pair of body projections 97 that engages the rails 88, and a pair of body claws 98 that engages the annular groove 90.

The fixing member 94 has an inside insertion hole 100 into which the opening tip portion 86*a* is inserted. The inner peripheral surface of the fixing member 94 is formed with a pair of engaging claws 101 that engages the cam grooves 89 at 180° to each other. Additionally, the upper end faces of the engaging claws 101 become inclined faces 91*a* substantially parallel to the inclined faces 101*a*.

A rotary ratchet mechanism 102 is provided between the inner peripheral surface of the holding portion 93*a* and the outer peripheral surface of the fixing member 94. The ratchet mechanism 102 includes a pair of ratchet claws 103 formed at 180° to each other on the outer peripheral surface of the fixing member 94, a pair of claw engagement grooves 104 (refer to FIG. 38) that is formed in the inner peripheral surface of the holding portion 93*a* and that the ratchet claws 103 engage, and ratchet gear teeth 105 (refer to FIG. 38) formed in the claw engagement grooves 104.

Figure 38:
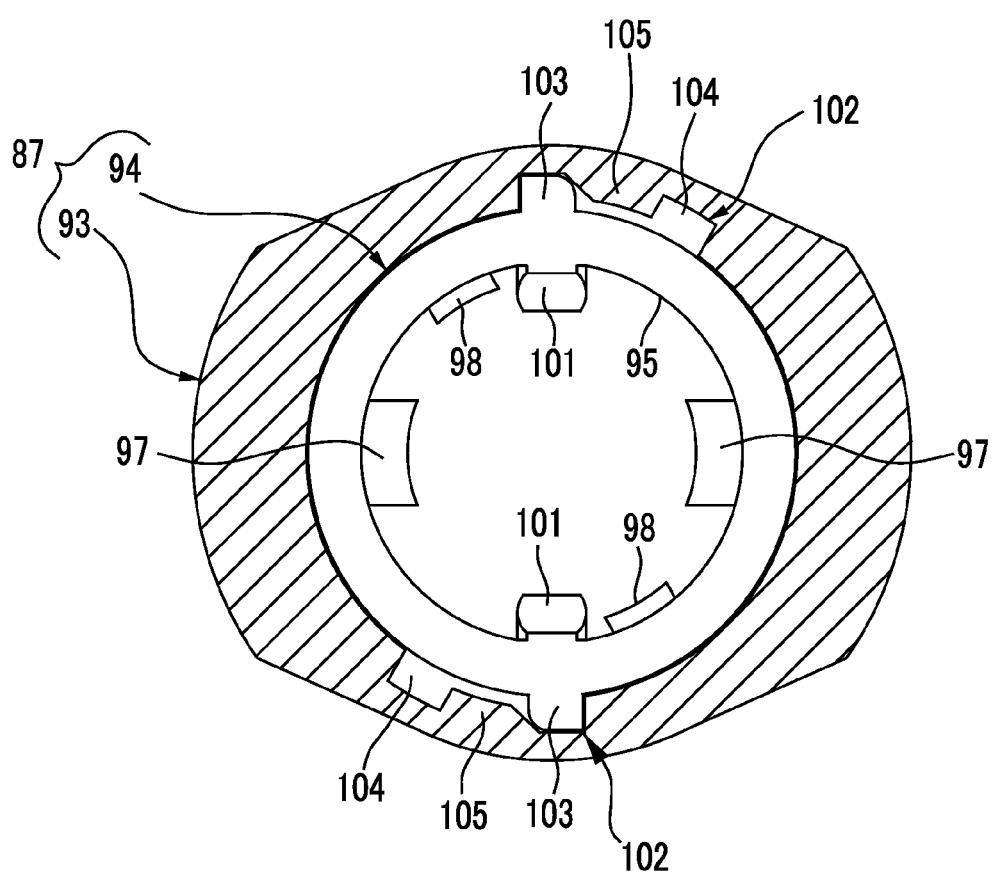
FIG. 38 is a cross-sectional view along line C-C in FIG. 36, showing a state where a fixing member is set at an attachment position.

The ratchet gear teeth 105 maintains a state where each ratchet claw 103 abuts on one end portion of each claw engagement groove 104 in the counterclockwise direction (refer to FIG. 38). Additionally, the ratchet gear teeth 105 allow each ratchet claw 103 to move to the other end portion of the claw engagement groove 104 in the clockwise direction, but stop the ratchet claw to returning to the one end portion from the other end portion.

Such a ratchet mechanism 102 allows the fixing member 27 to rotate in the clockwise direction, to move to a total of following two positions, that is, an attachment position, and a fixed position in order, but stops further movement to a position where the fixing member has moved once.

As shown in FIG. 38, the attachment position is a position when each ratchet claw 103 is at the one end portion of each claw engagement groove 104. In this attachment position, the body projections 97 and the engaging claws 101 are alternately arranged at pitch intervals of 90°. In addition, the fixing member 94 is set at the attachment position at the time of shipment of the forceps plug 87.

Figure 39:
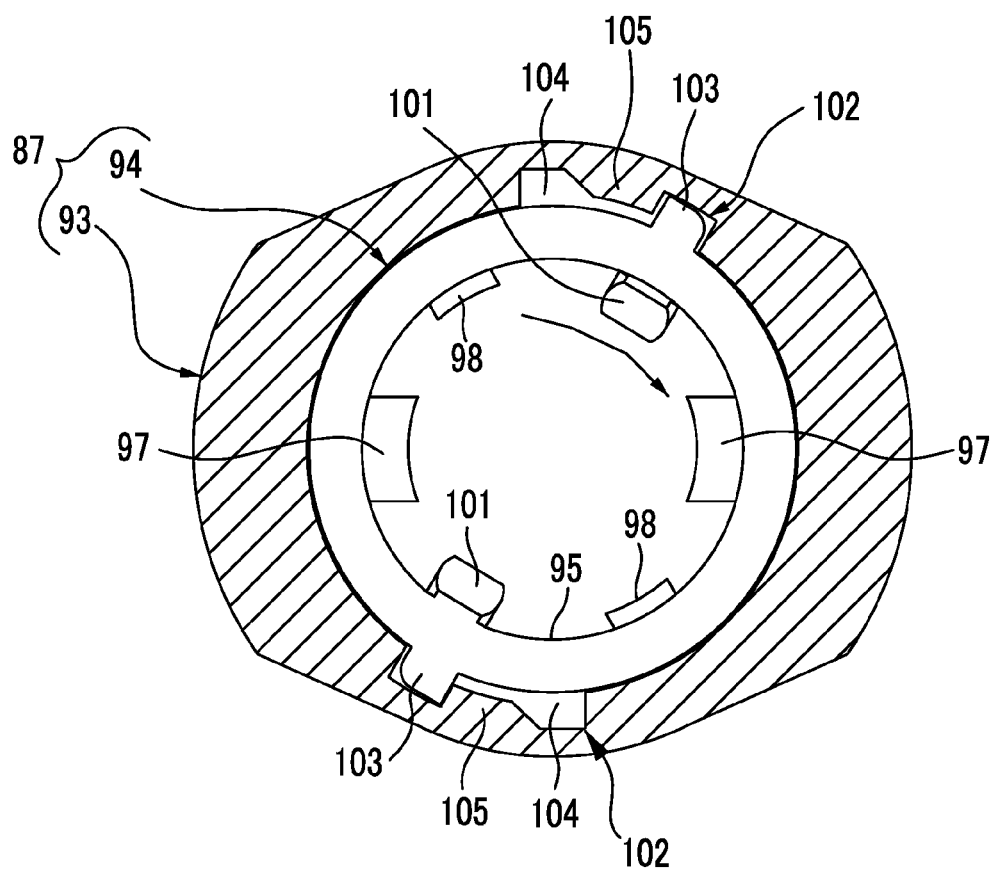
FIG. 39 is a cross-sectional view along line C-C in FIG. 36, showing a state where the fixing member is set at a fixed position.

As shown in FIG. 39, the fixed position is a position when each ratchet claw 103 is at the other end portion of each claw engagement groove 104. This fixed position is adjusted so that the engaging claws 101 and the engaged portions 89*b* are located on the same straight line parallel to the opening axial direction when the body projections 97 engage the rails 88.

Figure 40:
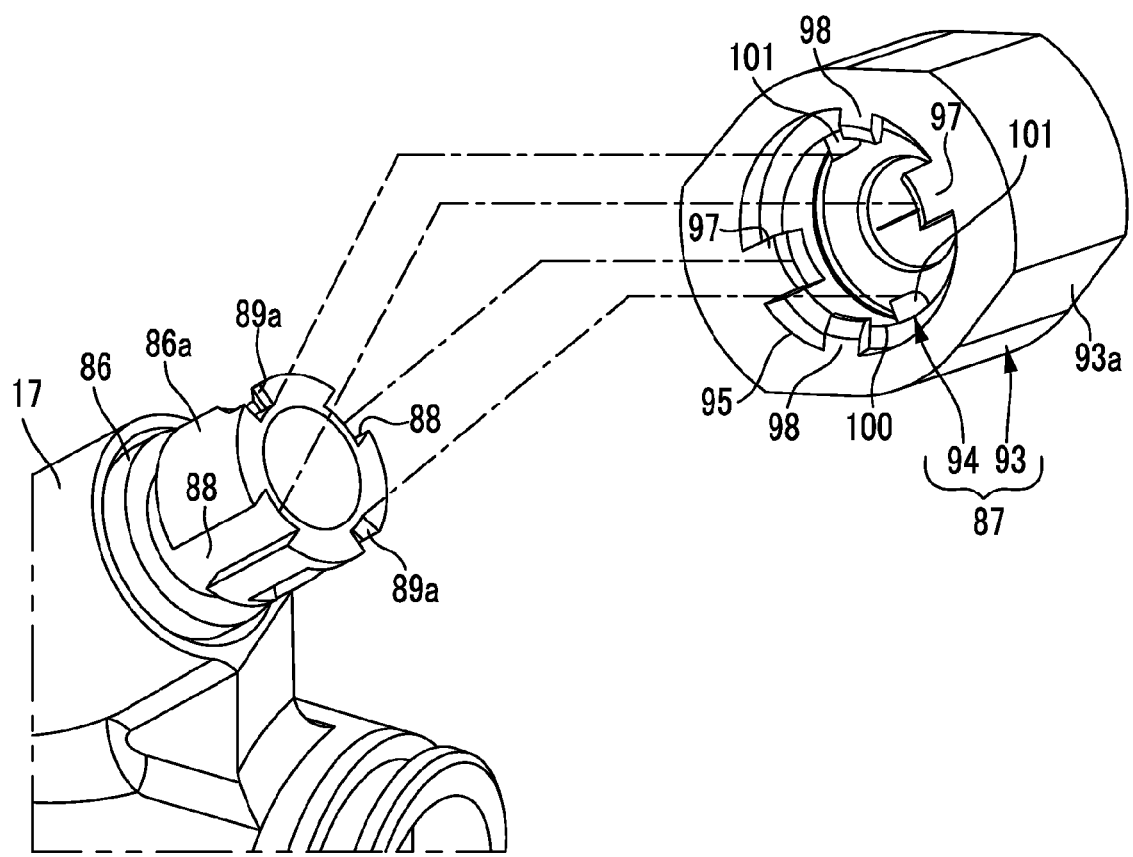
FIG. 40 is a perspective view of the plug before attachment to the opening.

Next, the attachment and removal processing of the forceps plug 87 of the above configuration will be described. In addition, the fixing member 94 is set at the attachment position in the stage of the shipment from a maker. As shown by the number (1) in parentheses of FIGS. 40 and 41, positioning of the forceps plug 87 is performed so that the body projections 97 and the engaging claws 101 are respectively located on the rails 88 and guide portions 89*a* of the opening tip portion 86*a*.

After the positioning of the forceps plug 87, the forceps plug 87 is pressed against the opening tip portion 86*a*. Thereby, the opening tip portion 86*a* is inserted into the outside insertion hole 95 and the inside insertion hole 100, and the body projections 97 and the engaging claws 101 are guided into the rails 88 and the guide portions 89*a*, respectively. When the pressing manipulation of the forceps plug 87 is continued, the forceps plug 87 moves downward along the rails 88 by the engagement between the body projections 97 and the rails 88.

Figure 41:
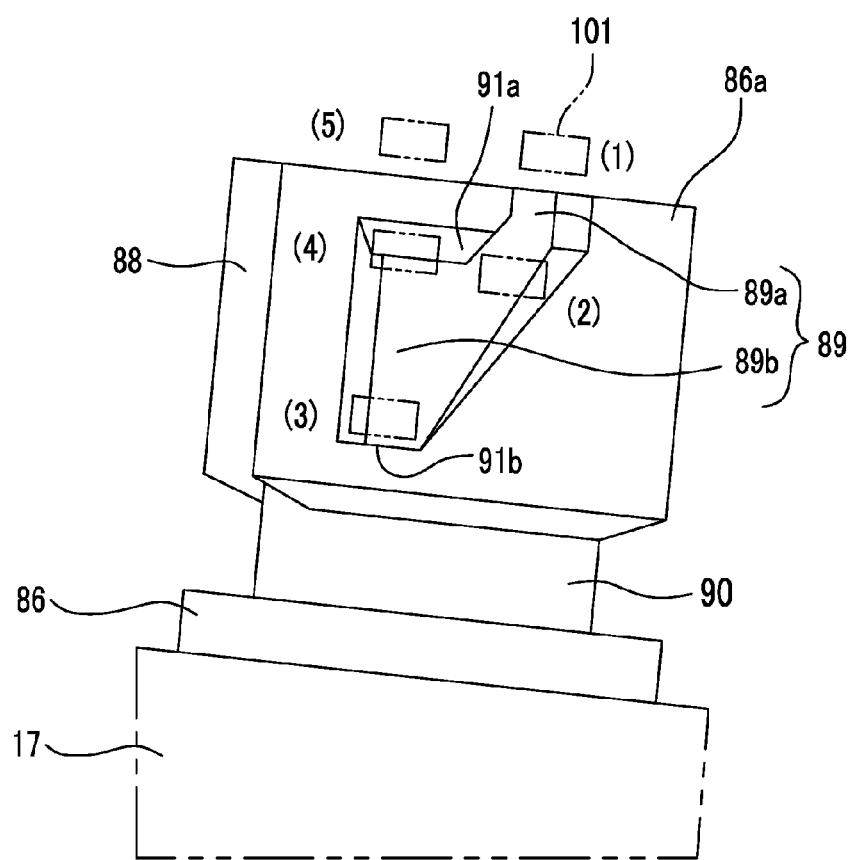
FIG. 41 is an explanatory view for explaining a movement path of an engaging claw that moves along a cam groove.

As shown by the number (2) in parentheses of FIG. 41, the engaging claws 101 move obliquely downward toward the engaged portions 89*b* along the guide portions 89*a* with the downward movement of the forceps plug 87. Thereby, a force is applied to the fixing member 94 in the clockwise direction. This force increases as the travel distance of the forceps plug 87 increases.

If the pressing manipulation of the forceps plug 87 is continued as shown by the number (3) in parentheses of FIG. 41, the ratchet claws 103 rise over the ratchet gear teeth 105, move to the other end portions of the claw engagement grooves 104, and the fixing member 94 is set at the fixed position. Additionally, the engaging claws 101 are guided into the engaged portions 89*b* from the guide portions 89*a*, and engage the engaged portions 89*b*. Then, if the engaging claws 101 abut on vertical faces 91*b* of the engaged portions 89*b*, further downward movement of the forceps plug 87 is regulated.

Figure 42:
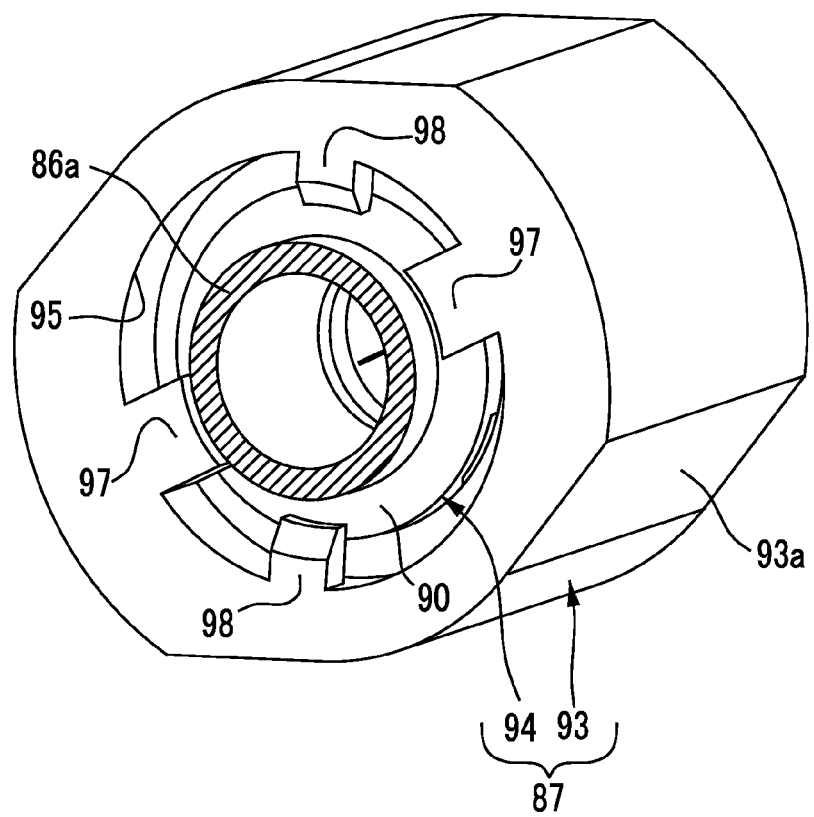
FIG. 42 is the perspective view of the forceps plug of the fifth embodiment fixed to the opening seen from the downward side.

Additionally, the body claws 98 engage the annular grooves 90 as shown in FIG. 42 until the engaging claws 101 abut on the vertical faces 91*b*. Thereby, the forceps plug 87 is fixed to the opening 86. Since the fixing member 94 can be automatically set at the fixed position when the forceps plug 87 is attached to the opening 86, a user can save manual setting time and efforts.

The attachment processing of the forceps plug 87 is completed above. Then, after the endoscopic examination and treatment are all completed, the removal processing of the forceps plug 87 is started.

Figure 43:
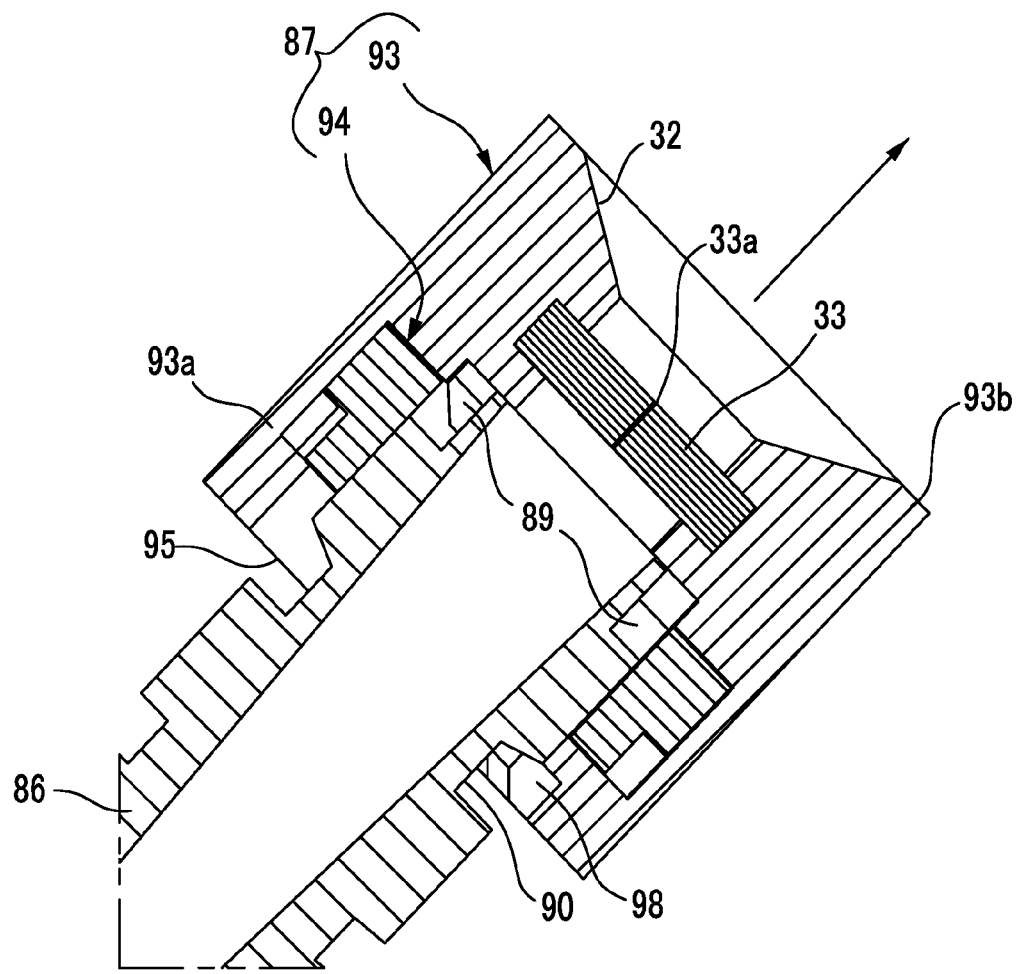
FIG. 43 is an explanatory view for explaining removal processing of the forceps plug of the fifth embodiment from the opening.

If the pulling manipulation of the forceps plug 87 is performed as shown in FIG. 43, the engagement between the body claws 98 and the annular groove 90 is released, and the forceps plug 87 moves upward along the rails 88.

If the pulling manipulation of the forceps plug 87 is continued, as shown by the number (4) in parentheses in FIG. 41, the inclined faces 101*a* of the engaging claws 101 are pressed against the inclined faces 91*a* of the engaged portions 89*b*, and the engaging claws 101 are deflected downward in the shape of a circular arc. Moreover, if the pulling manipulation is continued against the elastic force of the engaging claws 101, the engaging claws 101 ride over the outer peripheral surface of the opening tip portion 86*a* from the inclined faces 91*a*, and separate from the tip of the opening tip portion 86*a*. Thereby, the forceps plug 87 is removed from the opening 20.

Figure 44:
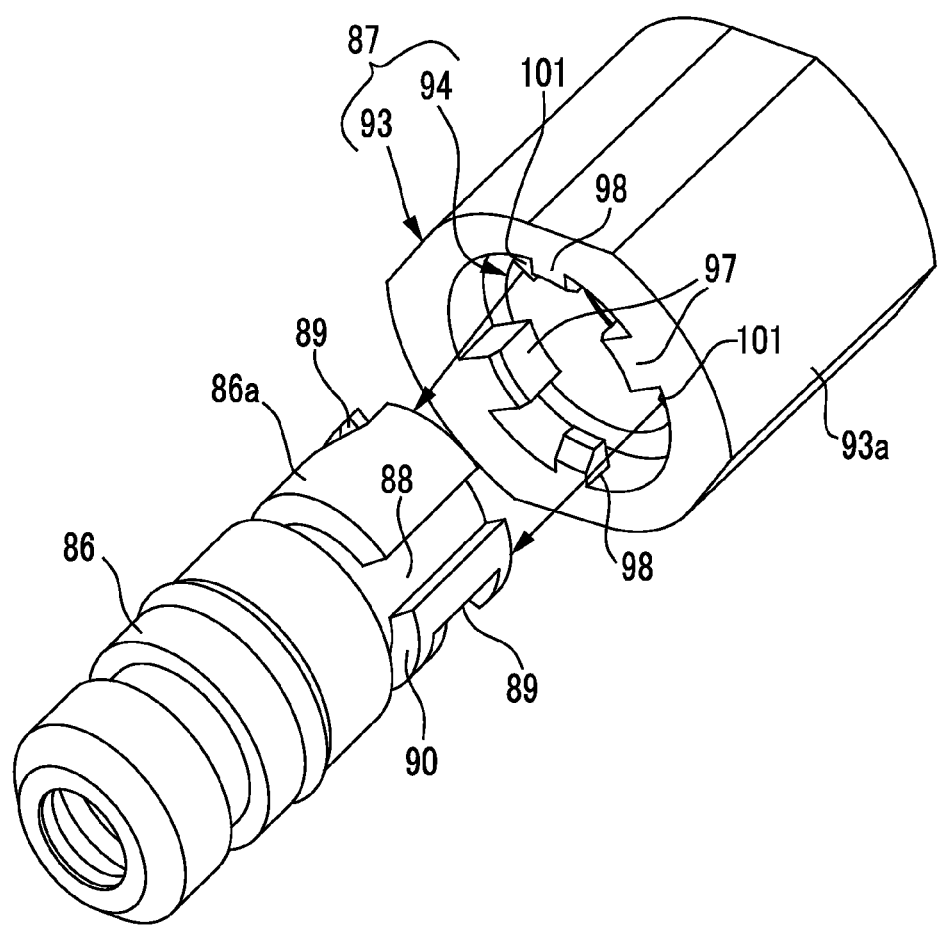
FIG. 44 is an explanatory view for explaining that reuse of the used forceps plug of the fifth embodiment becomes impossible.

As shown in FIG. 44, the fixing member 94 of the used forceps plug 87 cannot be returned to the attachment position from the fixed position by the ratchet mechanism 102. For this reason, if the alignment between the rails 88 and the body projections 97 is performed when the used forceps plug 87 is attached to the opening 86, positional deviation occurs between the guide portions 89*a* and the engaging claws 101. As a result, since the opening tip portion 86*a* interferes with the engaging claws 101, the forceps plug 87 cannot be attached to the opening 86. Thereby, since reuse of the forceps plug 87 is prevented, the same effects as the first embodiment are obtained.

In the above respective embodiments, description has been made taking the rotary or slide type ratchet mechanism as an example. However, in a structure where the fixing member cannot be returned to a position where the fixing member has moved once, the type or configuration is not particularly limited. Additionally, in the rotary ratchet mechanism of the above first, fourth, and fifth embodiments, the rotation of the fixing member in the clockwise direction is permitted and the rotation of the fixing member in the counterclockwise direction is stopped, and vice versa.

In the above respective embodiments, description has been made taking the forceps plug 21 to be attached to the opening 21 of the forceps port 17 as an example. However, the present invention can also be applied to a forceps plug to be directly mounted on the aperture of the forceps port 17.

In the above respective embodiments, description has been made taking the forceps plug 21 to be attached to the opening 20 that leads to the forceps channel 16 as an example. For example, however, the present invention can be applied to various kinds of channels disposed inside the endoscope 10, such as a suction channel and water supply and air supply channels, or a plug body for an endoscope to be attached to a opening portion that leads to a conduit.

In the above respective embodiments, description has been made by taking the endoscope 10 to be inserted into the trachea as an example. For example, however, the present invention can be applied to various endoscopes for medical purposes, such as a large-intestine endoscope to be inserted into the large intestine, an endoscope used for other applications, such as an industrial application, and the like.

What is claimed is:

1. A plug body provided on the external surface of an endoscope and attached to a tubular opening portion that leads to a channel within the endoscope, the plug body comprising:
   a tubular plug main body into which the opening portion is inserted;
   a tubular fixing member rotatably or slidably held in the plug main body, having an insertion hole into which the opening portion is inserted, and a claw provided on the inner peripheral surface that forms the insertion hole, and movable to respective positions including an engagement position where the claw engages an engaged portion provided at an outer periphery of the opening portion inserted into the insertion hole, and one or more non-engagement positions where the claw does not engage the engaged portion, and
   a ratchet mechanism provided in mutually opposed faces of the plug main body and the fixing member, permitting the fixing member to be moved to the respective positions in predetermined order, and stopping further movement of the fixing member to a position where the fixing member has moved once.

2. The plug body according to claim 1,
   wherein the non-engagement position includes a removal position when the plug main body is removed from the opening portion, and
   wherein the ratchet mechanism permits the fixing member to move in order of the engagement position and the removal position.

3. The plug body according to claim 2,
   wherein the fixing member is rotatably held on the outer periphery of the plug main body, and has an extending portion that extends to the downward side toward a deep side of an opening of the opening portion beyond the plug main body, and the extending portion is provided with the claw,
   wherein the non-engagement position includes an attachment position when the opening portion is inserted into the insertion hole, and
   wherein the ratchet mechanism permits the fixing member to be rotated in a predetermined rotational direction in order of the attachment position, the engagement position, and the removal position and stops the rotation of the fixing member in a reverse rotational direction opposite to the predetermined rotational direction.

4. The plug body according to claim 3,
   wherein the ratchet mechanism has a rotation stop that stops the fixing member from further rotating from the removal position to the predetermined rotational direction.

5. The plug body according to claim 3,
   wherein an unused mark indicating unused is provided at a position where the mark is exposed to the outside when the fixing member is at the attachment position, or at a position where the mark is covered with the plug main body when the fixing member is at the engagement position or the removal position, on the external surface of the fixing member.

6. The plug body according to claim 3,
   wherein a used mark indicating used is provided at a position where the mark is exposed to the outside when the fixing member is at the removal position, or at a position where the mark is covered with the plug main body when the fixing member is at the attachment position or the engagement position, on the external surface of the fixing member.

7. The plug body according to claim 2,
   wherein the fixing member is held on the inner periphery of the plug main body so as to be slidable along the axial direction of the opening portion, and the removal position is a position offset to the downward side toward the deep side of an opening of the opening portion beyond the engagement position, and
   wherein the inner periphery of the plug main body is provided with an engagement releasing portion that releases the engagement between the claw and the engaged portion when the fixing member has relatively moved to the removal position from the engagement position with the removal manipulation of pulling the plug main body in an upward direction toward the near side of the opening of the opening portion.

8. The plug body according to claim 7,
   wherein the fixing member has an arm portion formed by cutting out a portion of the fixing member, and extending a considerable length in the axial direction, and having an end on the downward side as a free end, and the free end is provided with the claw,
   wherein the engagement releasing portion has a shape that protrudes toward the claw from the position offset to the downward side with respect to the claw,
   wherein when the fixing member has moved to the removal position, the engagement between the claw and the engaged portion is released as the engagement releasing portion presses the claw to elastically deform the arm portion in a direction in which the claw is kept away from the outer periphery of the opening portion.

9. The plug body according to claim 7,
   wherein the fixing member has an arm portion formed by cutting out a portion of the fixing member, and extending a considerable length in the axial direction, and having an end on the downward side as a free end,
   wherein one face of the free end facing the opening portion is provided with the claw, and the other face opposite to the one face is provided with a protruding portion that protrudes toward the inner periphery of the plug main body, and receives the pressure from the inner periphery to elastically deform the arm portion in a direction toward the outer periphery of the opening portion, thereby maintaining a state where the claw is engaged with the engaged portion, wherein the engagement releasing portion is a fitting groove formed in the inner periphery of the plug main body and engaged with the protruding portion when the fixing member has moved to the removal position, and wherein the engagement between the claw and the engaged portion is released as the arm portion restores to original shape of the arm portion when the protruding portion fits to the fitting groove.

10. The plug body according to claim 1, wherein the fixing member is rotatably held on the inner periphery or outer periphery of the plug main body, wherein the non-engagement position includes an attachment position when the opening portion is inserted into the plug main body, wherein the ratchet mechanism permits the fixing member to be rotated in a predetermined rotational direction in order of the attachment position and the engagement position, and stops the rotation of the fixing member in a reverse rotational direction opposite to the predetermined rotational direction, and wherein when the removal manipulation of pulling the plug main body to the upward side toward the near side of the opening of the opening portion is performed in a state where the fixing member is at the engagement position, the claw is pressed against and deflected by the engaged portion located on the upward side of the claw, and thereby, the engagement between the claw and the engaged portion is released to remove the plug main body from the opening portion.

11. The plug body according to claim 10, wherein the fixing member has an extending portion that is rotatably held on the outer periphery of the plug main body and extends closer to the direction of the opening portion than the plug main body, and the claw is provided at the extending portion.

12. The plug body according to claim 10, wherein the fixing member is rotatably held on the inner periphery of the plug main body, wherein the claw engages a guide groove that extends in an oblique direction from a opening portion tip position offset in the reverse rotational direction with respect to the engaged portion to the engaged portion, in the tip of the opening portion when the fixing member is at the attachment position, and wherein when the attachment manipulation of pressing the plug main body against the opening portion after the engagement between the claw and the guide groove is performed, the claw moves to the engaged portion along the guide groove, and the fixing member rotates to the engagement position from the attachment position with the movement of the claw.

13. The plug body according to claim 10, wherein the ratchet mechanism is provided with a rotation stop that stops the fixing member from further rotating from the engagement position to the predetermined rotational direction.

14. The plug body according to claim 11, wherein the ratchet mechanism is provided with a rotation stop that stops the fixing member from further rotating from the engagement position to the predetermined rotational direction.

15. An endoscope comprising:

a manipulating part connected to a base end portion of an insertion part to be inserted into a subject;

a tubular opening portion that is provided in the manipulating part and leads to a channel inserted into the insertion part; and the plug body according to claim 1 attached to the opening portion.

16. An endoscope comprising:

a manipulating part connected to a base end portion of an insertion part to be inserted into a subject;

a tubular opening portion that is provided in the manipulating part and leads to a channel inserted into the insertion part; and the plug body according to claim 2 attached to the opening portion.

17. An endoscope comprising:

a manipulating part connected to a base end portion of an insertion part to be inserted into a subject;

a tubular opening portion that is provided in the manipulating part and leads to a channel inserted into the insertion part; and the plug body according to claim 3 attached to the opening portion.

18. An endoscope comprising:

a manipulating part connected to a base end portion of an insertion part to be inserted into a subject;

a tubular opening portion that is provided in the manipulating part and leads to a channel inserted into the insertion part; and the plug body according to claim 4 attached to the opening portion.

19. An endoscope comprising:

a manipulating part connected to a base end portion of an insertion part to be inserted into a subject;

a tubular opening portion that is provided in the manipulating part and leads to a channel inserted into the insertion part; and the plug body according to claim 5 attached to the opening portion.

20. An endoscope comprising:

a manipulating part connected to a base end portion of an insertion part to be inserted into a subject;

a tubular opening portion that is provided in the manipulating part and leads to a channel inserted into the insertion part; and the plug body according to claim 6 attached to the opening portion.

* * * * *